(12) United States Patent
McNamara et al.

(10) Patent No.: US 10,588,527 B2
(45) Date of Patent: Mar. 17, 2020

(54) CARDIAC ARRHYTHMIA REPORT

(75) Inventors: Anna McNamara, Susquehanna, PA (US); Jonathan Newbrough, San Diego, CA (US); Charles Gropper, Mission Viejo, CA (US); Aaron Goldmuntz, Lafayette Hill, PA (US); Yachuan Pu, Dana Point, CA (US)

(73) Assignee: Braemar Manufacturing, LLC, Eagan, MN (US)

( * ) Notice: Subject to any disclaimer, the term of this patent is extended or adjusted under 35 U.S.C. 154(b) by 1034 days.

(21) Appl. No.: 12/425,361

(22) Filed: Apr. 16, 2009

(65) Prior Publication Data
US 2010/0268103 A1    Oct. 21, 2010

(51) Int. Cl.
*A61B 5/0402*  (2006.01)
*G16H 15/00*  (2018.01)

(52) U.S. Cl.
CPC ............ *A61B 5/0402* (2013.01); *G16H 15/00* (2018.01)

(58) Field of Classification Search
CPC . G06F 19/3487; A61B 5/0402; A61B 5/7264; A61B 5/0452; A61B 5/0006; A61B 5/00464
USPC ..... 600/512–519, 522, 523, 373–375; 607/4, 607/5, 14, 17, 18, 25, 26, 119–123
See application file for complete search history.

(56) References Cited

U.S. PATENT DOCUMENTS

| | | |
|---|---|---|
| 4,622,979 A | 11/1986 | Katchis et al. |
| 4,630,204 A | 12/1986 | Mortara |
| 4,920,489 A | 4/1990 | Hubelbank et al. |
| 4,938,228 A | 7/1990 | Righter et al. |
| 4,951,681 A | 8/1990 | Mortara |
| 4,958,641 A | 9/1990 | Digby et al. |
| 4,977,899 A | 12/1990 | Digby et al. |
| D326,716 S | 6/1992 | Mortara |
| 5,191,891 A | 3/1993 | Righter |
| 5,197,479 A | 3/1993 | Hubelbank et al. |

(Continued)

FOREIGN PATENT DOCUMENTS

| | | |
|---|---|---|
| EP | 0 360 412 | 3/1995 |
| JP | 2003-599 A | 1/2004 |

OTHER PUBLICATIONS

Biomedical Computer Laboratory, Institute for Biomedical Computing, Washington University, "Progress Report No. 21," Jul. 1, 1984-Jun. 30, 1985, 164 pages.

(Continued)

*Primary Examiner* — Lindsey G Wehrheim
(74) *Attorney, Agent, or Firm* — Chang B. Hong, Esq.

(57) ABSTRACT

Systems, devices, methods, and techniques relating to generating and presenting information related to heart rate data. In one aspect, a system includes a monitoring device configured to obtain physiological data for a living being and to generate annotation data based on the physiological data for a total time period, a processing system configured to obtain the annotation data via a communication channel from the monitoring device and to generate for display based on the annotation data a daily patient report that includes, a chart showing summary statistical data for a proportion of a total monitored time period spent in cardiac arrhythmia for each of a plurality of days and summary statistical data for a proportion of the total monitored time period not spent in cardiac arrhythmia for each of the plurality of days.

39 Claims, 9 Drawing Sheets

(56) References Cited

U.S. PATENT DOCUMENTS

| | | | |
|---|---|---|---|
| 5,217,021 A | 6/1993 | Steinhaus et al. | |
| 5,226,425 A | 7/1993 | Righter | |
| 5,365,935 A | 11/1994 | Righter et al. | |
| 5,421,342 A | 6/1995 | Mortara | |
| 5,490,515 A | 2/1996 | Mortara | |
| 5,513,645 A | 5/1996 | Jacobson et al. | |
| 5,522,396 A | 6/1996 | Langer et al. | |
| 5,546,950 A | 8/1996 | Schoeckert et al. | |
| 5,581,369 A | 12/1996 | Righter et al. | |
| D377,983 S | 2/1997 | Sabri | |
| 5,634,468 A | 6/1997 | Platt et al. | |
| 5,676,153 A | 10/1997 | Smith et al. | |
| 5,678,562 A | 10/1997 | Sellers | |
| 5,704,351 A | 1/1998 | Mortara et al. | |
| 5,730,143 A | 3/1998 | Schwarzberg | |
| 5,868,680 A | 2/1999 | Steiner et al. | |
| 5,931,791 A | 8/1999 | Saltzstein et al. | |
| 5,942,986 A | 8/1999 | Shabot et al. | |
| 5,948,005 A * | 9/1999 | Valikai et al. | 607/32 |
| D414,870 S | 10/1999 | Saltzstein et al. | |
| 5,966,692 A | 10/1999 | Langer et al. | |
| 6,064,906 A | 5/2000 | Langberg et al. | |
| 6,102,856 A | 8/2000 | Groff et al. | |
| 6,246,907 B1 | 6/2001 | Lin et al. | |
| 6,287,252 B1 | 9/2001 | Lugo | |
| 6,302,844 B1 | 10/2001 | Walker et al. | |
| 6,366,871 B1 | 4/2002 | Geva | |
| 6,409,661 B1 | 6/2002 | Murphy | |
| 6,411,840 B1 | 6/2002 | Bardy | |
| 6,418,340 B1 | 7/2002 | Conley et al. | |
| 6,449,504 B1 | 9/2002 | Conley et al. | |
| 6,485,429 B2 | 11/2002 | Forstner | |
| 6,524,239 B1 | 2/2003 | Reed et al. | |
| 6,564,077 B2 | 5/2003 | Mortara | |
| 6,583,796 B2 * | 6/2003 | Jamar | A61B 5/044 600/525 |
| 6,687,685 B1 | 2/2004 | Sadeghi et al. | |
| 6,697,655 B2 | 2/2004 | Sueppel et al. | |
| 6,937,887 B2 | 8/2005 | Bock | |
| 7,001,334 B2 | 2/2006 | Reed et al. | |
| 7,212,850 B2 * | 5/2007 | Prystowsky et al. | 600/523 |
| 7,223,234 B2 | 5/2007 | Stupp et al. | |
| 7,311,665 B2 | 12/2007 | Hawthorne et al. | |
| 7,542,878 B2 | 6/2009 | Nanikashvili | |
| 2002/0099303 A1 | 7/2002 | Bardy | |
| 2002/0128804 A1 | 9/2002 | Geva | |
| 2002/0173727 A1 | 11/2002 | Bardy | |
| 2003/0028442 A1 | 2/2003 | Wagstaff et al. | |
| 2003/0069486 A1 | 4/2003 | Sueppel et al. | |
| 2003/0069487 A1 | 4/2003 | Mortara | |
| 2004/0010201 A1 | 1/2004 | Korzinov et al. | |
| 2005/0119833 A1 | 6/2005 | Nanikashvili | |
| 2005/0203349 A1 | 9/2005 | Nanikashvili | |
| 2007/0100213 A1 | 5/2007 | Dossas et al. | |
| 2007/0191723 A1 | 8/2007 | Prystowsky et al. | |
| 2007/0232455 A1 * | 10/2007 | Hanoun | 482/8 |
| 2008/0071580 A1 * | 3/2008 | Marcus et al. | 705/3 |

OTHER PUBLICATIONS

Savi Wireless—Mobile Cardiac Telemetry Brochure, published by at least May 2009, 12 pages, Medicomp, Melbourne, Florida.

Jan Galuszka et al., "Assessment of Spectral Analysis of Heart Rate Variability in Patients With History of Atrial Fibrillation by Means of Age-Dependent Parameters", Biomed. Papers 146(2), 81-85 (2002).

Med Monitoring Systems, Inc. (Holter, Spiro, DMS, ECG, EKG, APB), http://www.medmonitoringsystems.com/holtertestanalysis2.html.

Massimo Santini et al., "Atrial Fibrillation: The Role of Atrial Defibrillation", Journal of Interventional Cardiac Electrophysiology 9, 229-233, 2003.

Mar. 10, 2008; CA2544926; Office Action from CA Intellectual Property Office, (CA counter-part).

Jun. 30, 2009: JP2007-516024; AOffice Action from JP Intellectual Property Office, (JP counter-part).

* cited by examiner

Report ID: 888888  Daily Patient Report  4/18/2009

| Patient Name: John Doe<br>Date of Birth: 01/01/1929 Gender: Male<br>Patient Phone: (858) 555-1212<br>ID Number: 999-99-9999<br>Medical Record: 12345 | Prescribing Physician: James Q. Doctor, MD<br>Small Town Medical Group<br>123 Main Street<br>San Diego, CA 92109<br>Referring Physician: |

Diagnosis (ICD-9): 427.31 Atrial fibrillation   Ablation Monitoring Schedule: 3, 9 months
Date of Ablation: 1-15-2009

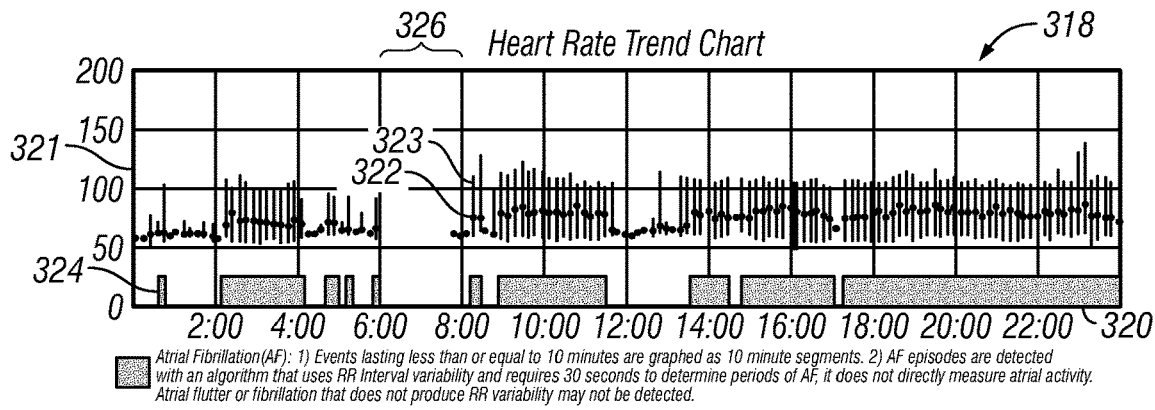

Atrial Fibrillation(AF): 1) Events lasting less than or equal to 10 minutes are graphed as 10 minute segments. 2) AF episodes are detected with an algorithm that uses RR Interval variability and requires 30 seconds to determine periods of AF, it does not directly measure atrial activity. Atrial flutter or fibrillation that does not produce RR variability may not be detected.

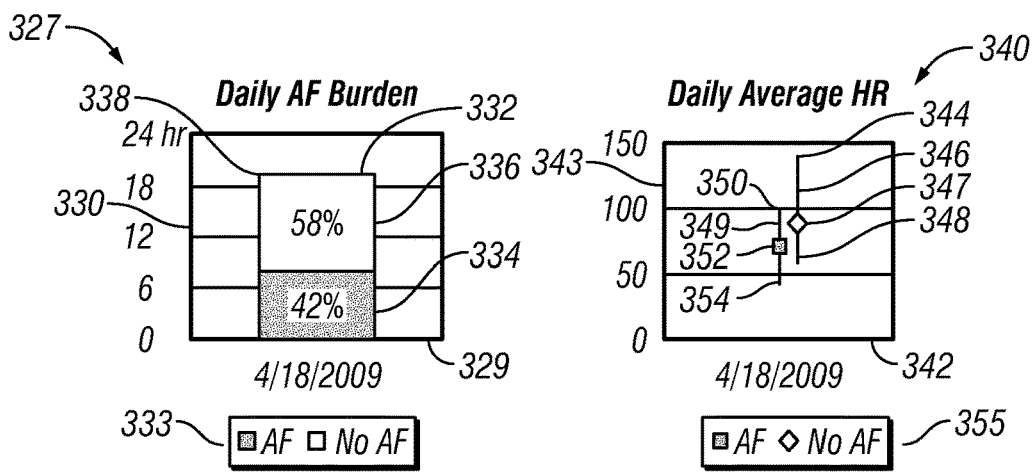

AF Statistics for 4/18/2009

| Total Time Monitored | 19 hours 30 minutes |
| Time in Atrial Fibrillation | 8 hours 11 minutes |
| Highest Heart Rate in AF | 139 bpm at 23:03 |
| Longest AF Episode | 4 hours 12 minutes at 17:42 |
| Average HR in AF | 76 bpm |
| Average HR not in AF | 61 bpm |

Doe, John  MRN 12345  4/18/2008

FIG. 3

Report ID: 888888   Daily Patient Report   4/22/2009

| | |
|---|---|
| Patient Name: John Doe<br>Date of Birth: 01/01/1929 Gender: Male<br>Patient Phone: (858) 555-1212<br>ID Number: 999-99-9999<br>Medical Record: 12345 | Prescribing Physician: James Q. Doctor, MD<br>   Small Town Medical Group<br>   123 Main Street<br>   San Diego, CA 92109<br>Referring Physician: |

Diagnosis (ICD-9): 427.31 Atrial fibrillation
Date of Ablation: 1-15-2009

Ablation Monitoring Schedule: 3,9 months

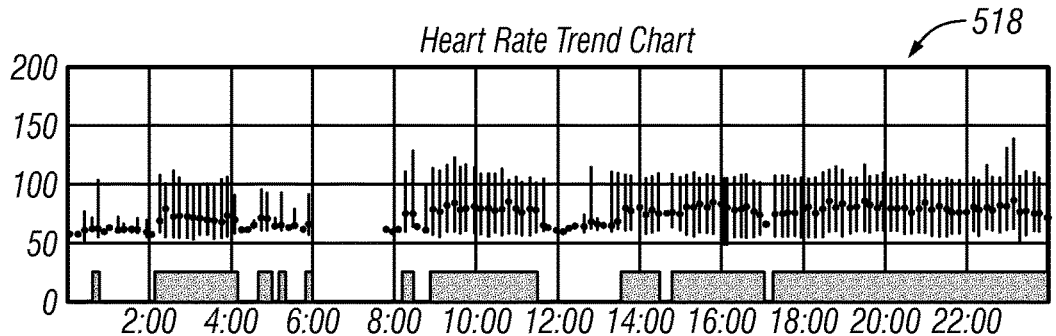

Atrial Fibrillation(AF): 1) Events lasting less than or equal to 10 minutes are graphed as 10 minute segments. 2) AF episodes are detected with an algorithm that uses RR Interval variability and requires 30 seconds to determine periods of AF, it does not directly measure atrial activity. Atrial flutter or fibrillation that does not produce RR variability may not be detected.

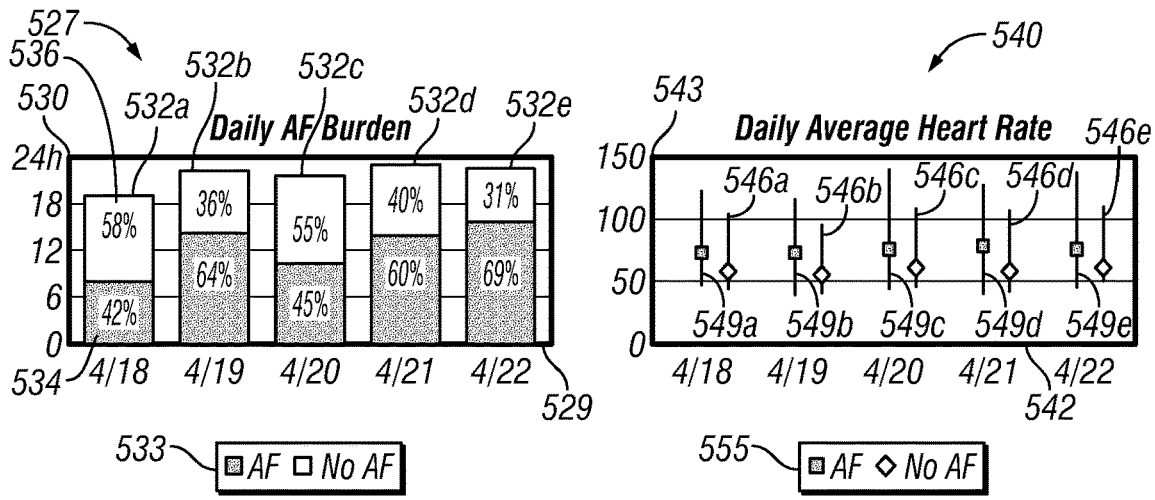

AF Statistics for 4/22/2009

| | |
|---|---|
| Total Time Monitored | 22 hours 6 minutes |
| Time in Atrial Fibrillation | 15 hours 24 minutes |
| Highest Heart Rate in AF | 139 bpm at 23:03 |
| Longest AF Episode | 4 hours 12 minutes at 17:42 |
| Average HR in AF | 76 bpm |
| Average HR not in AF | 61 bpm |

FIG. 5

Report ID: 888888  End of Service Summary Report  5/1/2009

| Patient Name: John Doe<br>Date of Birth: 01/01/1929 Gender: Male<br>Patient Phone: (858) 555-1212<br>ID Number: 999-99-9999<br>Medical Record: 12345 | Prescribing Physician: James Q. Doctor, MD<br>Small Town Medical Group<br>123 Main Street<br>San Diego, CA 92109<br>Refering Physician: |
|---|---|

Diagnosis (ICD-9): 427.31 Atrial fibrillation
Date of Ablation: 1-15-2009    Ablation Monitoring Schedule: 3,9 months

*Atrial Fibrillation Summary*

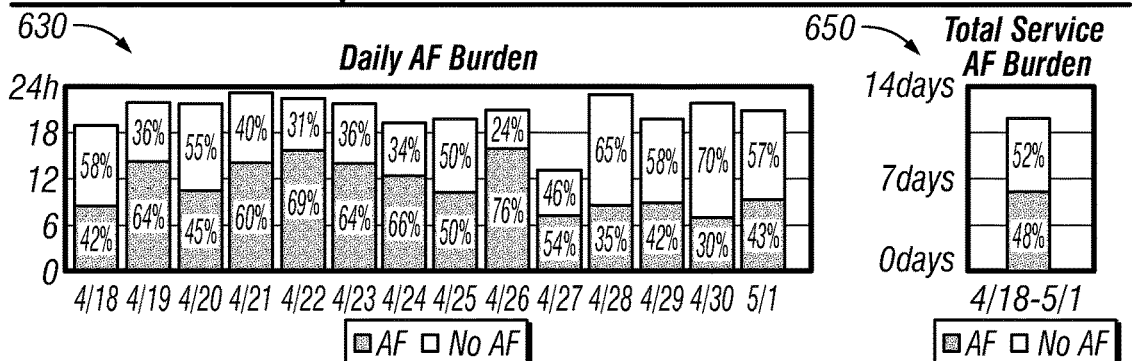

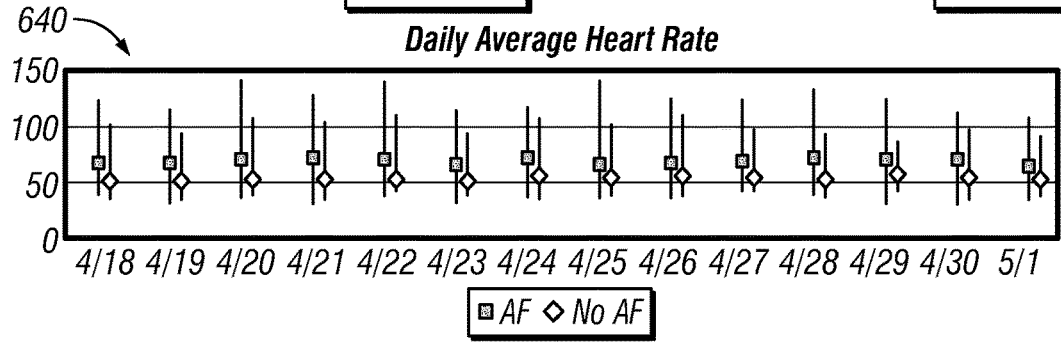

Service Summary Statistics for 4/18/2009 - 5/1/2009

| Total Time Monitored | 262 hours 6 minutes |
| Time in Atrial Fibrillation | 125 hours 48 minutes |
| Highest Heart Rate in AF | 145 bpm on 4/25 at 12:42 |
| Longest AF Episode | 4 hours 12 minutes on 4/18 at 17:42 |
| Average HR in AF | 77 bpm |
| Average HR not in AF | 62 bpm |

Service Summary

Emergency /Urgent Reports

| Date | Symptom | Findings | HR |
|---|---|---|---|
| 4/18/2008 | auto | Urgent-Normal Sinus Rythm with New Onset Atrial Fibrillation/Flutter, Dr. Doctor notified on 4/18/09 09:34 | 94 |
| 4/20/2008 | auto | Urgent-Atrial Fibrillation/Flutter, Dr. Doctor notified on 4/20/09 18:56 | 140 |
| 4/25/2008 | auto | Urgent-Atrial Fibrillation/Flutter, Dr. Doctor notified on 4/25/09 17:23 | 142 |

FIG. 6

Patient: Sample Patient  — 710   SSN: 555-55-5555   MRN: 765432

Daily Reports Billable

| Date | Symptom | Findings | HR |
|---|---|---|---|
| 05/03/2006 | auto | Urgent-Normal Sinus Rythm with First Atrial Fibrillation/Flutter>10 seconds Onset, Dr. Doc notified on 04/03/06 at 18:56 | 94 |
| 05/03/2006 | auto | Urgent-Atrial Fibrillation/Flutter Onset, Dr. Doc notified on 04/03/06 at 18:56 | 158 |
| 05/03/2006 | auto | Urgent-Atrial Fibrillation/Flutter >10 seconds Offset, into Normal Sinus Rythm, Dr. Doc notified on 04/03/06 at 18:56 | 84 |
| 05/04/2006 | auto | Normal Sinus Rythm with PSVT Onset 16 beats, 131 bpm | 67 |
| 05/04/2006 | auto | PSVT Offset 16 beats, 131 bpm into Sinus Rythm | 66 |
| 05/05/2006 | Light Headed, Fatigue | Normal Sinus Rythm with PSVT Onset 23 beats, 163 bpm | 85 |
| 05/05/2006 | Light Headed, Fatigue | PSVT Offset 23 beats, 163 bpm into Sinus Bradycardia | 53 |
| 05/06/2006 | auto | Normal Sinus Rythm with PSVT Onset 9 beats, 145 bpm | 69 |
| 05/06/2006 | auto | PSVT Offset 9 beats, 145 bpm into Sinus Rythm | 86 |
| 05/07/2006 | auto | Sinus Arrhythmia with PACs | 76 |
| 05/07/2006 | auto | Normal Sinus Rythm with PSVT Onset, 13 beats, 141 bpm | 84 |
| 05/07/2006 | auto | PSVT Offset, 13 beats, 144 bpm, into Sinus Rythm | 78 |
| 05/08/2006 | Light Headed | Normal Sinus Rhythm with PAC and PVC | 94 |
| 05/08/2006 | auto | Normal Sinus Rythm with PSVT Onset, 11 beats, 166 bpm | 71 |
| 05/08/2006 | auto | PSVT Offset, 11 beats, 166 bpm, into Sinus Rythm | 71 |
| 05/09/2006 | auto | Normal Sinus Rythm with Atrial Fibrillation/Flutter Run(s) less than 10 seconds Onset | 93 |
| 05/09/2006 | auto | Atrial Fibrillation/Flutter Run(s) less than 10 seconds Offset into Normal Sinus Rythm | 84 |

Interpretation — 725

Treatment Plan — 735

*Physician Signature* _____

FIG. 7

CARDIAC ARRHYTHMIA REPORT

BACKGROUND

The present application describes systems and techniques relating to processing and presenting arrhythmia event information from physiological data, for example, presenting atrial fibrillation events and related data in a patient report to a medical practitioner.

Over the years, various devices have been used for monitoring hearts in living beings. Additionally, systems have been used to collect and report on heart information obtained from patients.

SUMMARY

In a first aspect, a machine implemented method includes obtaining data associated with cardiac arrhythmia events and heart rate in a monitored living being; determining a total time period of monitoring for a first day; calculating from the obtained data a proportion of the total time period for the first day spent in cardiac arrhythmia; and generating for display a patient report, including adding to the patient report information related to: the total time period for the first day, and the proportion of the total time period for the first day spent in cardiac arrhythmia.

Implementations can include any, all, or none of the following features. Obtaining data associated with cardiac arrhythmia events can include obtaining data associated with atrial fibrillation events; calculating from the obtained data a proportion of the total time period for the first day spent in cardiac arrhythmia can include calculating from the obtained data a proportion of the total time period for the first day spent in atrial fibrillation; and adding to the patient report information related to the proportion of the total time period for the first day spent in cardiac arrhythmia can include adding to the patient report information related to the proportion of the total time period for the first day spent in atrial fibrillation. The machine-implemented method can include calculating from the obtained data a proportion of the total time period for the first day not spent in cardiac arrhythmia; and wherein adding to the patient report information can include adding to the patient report information related to the proportion of the total time period for the first day not spent in cardiac arrhythmia. Adding to the patient report information can include adding information related to a chart can including: a graph, can including a first axis representing a duration of time and a second axis representing date; a bar on the graph having a dimension parallel to the first axis wherein the length of the dimension depicts the total time period of monitoring for the first day; a first color on the bar and a second color on the bar; wherein the amount of the first color with respect to the second color can be proportional to the proportion of the total time period for the first day spent in cardiac arrhythmia; and wherein the amount of the second color with respect to the first color can be proportional to the proportion of the total time period for the first day not spent in cardiac arrhythmia.

The machine-implemented method can include calculating from the obtained data a maximum, a minimum, and an average heart rate for the proportion of the total time period for the first day spent in cardiac arrhythmia; calculating from the obtained data a maximum, a minimum, and an average heart rate for the proportion of the total time period for the first day not spent in cardiac arrhythmia; and wherein adding to the patient report information can include adding information related to: the maximum, the minimum, and the average heart rate calculated for the proportion of the total time period spent in cardiac arrhythmia; and the maximum, the minimum, and the average heart rate calculated for the proportion of the total time period not spent in cardiac arrhythmia.

Adding to the patient report information can include adding information related to a chart including: a graph, including a first axis representing heart rate and a second axis representing date of monitoring; a first bar on the graph having a dimension parallel to the first axis; the first bar having a first end proximal to the second axis and a second end distal to the second axis, wherein the first end represents the minimum heart rate and the second end represents the maximum heart calculated for the proportion of the total time period spent in cardiac arrhythmia; a first indicator on the first bar for indicating the average heart rate calculated for the proportion of the total time period spent in cardiac arrhythmia; a second bar on the graph having a dimension parallel to the first axis; the second bar having a first end proximal to the second axis and a second end distal to the second axis, wherein the first end represents the minimum heart rate and the second end represents the maximum heart calculated for the proportion of the total time period not spent in cardiac arrhythmia; and a second indicator on the second bar for indicating the average heart rate calculated for the proportion of the total time period not spent in cardiac arrhythmia.

Adding information related to a chart can include adding information related to the first and second indicator wherein the first indicator can have a different color or shape than the second indicator. The machine-implemented method can include determining a total time period of monitoring for a second or more days; calculating from the obtained data a proportion of the total time period spent in cardiac arrhythmia for each of the second or more days; and wherein adding information to the patient report can include adding information related to: the total time period for each of the second or more days; and the proportion of the total time period spent in cardiac arrhythmia for each of the second or more days. The machine-implemented method can include calculating from the obtained data a proportion of the total time period not spent in cardiac arrhythmia for each of the second or more days; and wherein adding to the patient report information can include adding information related to the proportion of the total time period not spent in cardiac arrhythmia for each of the second or more days.

Obtaining data associated with cardiac arrhythmia events can include obtaining data associated with the on-set and off-set of a cardiac arrhythmia event. The machine-implemented method can include receiving human assessment data associated with the cardiac arrhythmia events; and modifying the proportion of the total time period for the first day spent in cardiac arrhythmia based on the human assessment data. The machine-implemented method can include calculating one or more of a total time spent in cardiac arrhythmia, a maximum heart rate for the proportion of the total time period spent in cardiac arrhythmia, a longest cardiac arrhythmia episode, an average heart rate for the proportion of the total time period spent in cardiac arrhythmia, an average heart rate for the proportion of the total time period not spent in cardiac arrhythmia; and wherein adding to the patient report information can include adding information related to one or more of the total time monitored, the total time spent in cardiac arrhythmia, the maximum heart rate for the proportion of the total time period spent in cardiac arrhythmia, the longest cardiac arrhythmia episode, the average heart rate for the proportion of the total time period spent in cardiac arrhythmia, and the average heart rate for the proportion of the total time period not spent in cardiac arrhythmia.

In a second aspect, a system includes one or more computers and a computer-readable storage device having a computer program product encoded therein, the computer program product operable to cause the one or more computers to perform operations including: obtaining data associated with cardiac arrhythmia events and heart rate in a monitored living being; determining a total time period of monitoring for a first day; calculating from the obtained data a proportion of the total time period for the first day spent in cardiac arrhythmia; and generating for display a patient report including adding to the patient report information related to: the total time period for the first day and the proportion of the total time period for the first day spent in cardiac arrhythmia.

Implementations can include any, all, or none of the following features. Obtaining data associated with cardiac arrhythmia events can include obtaining data associated with atrial fibrillation events; calculating from the obtained data a proportion of the total time period for the first day spent in cardiac arrhythmia can include calculating from the obtained data a proportion of the total time period for the first day spent in atrial fibrillation; and adding to the patient report information related to the proportion of the total time period for the first day spent in cardiac arrhythmia can include adding to the patient report information related to the proportion of the total time period for the first day spent in atrial fibrillation. The computer-readable storage device can be further operable to cause the one or more computers to perform operations including calculating from the obtained data a proportion of the total time period for the first day not spent in cardiac arrhythmia; and adding to the patient report information can include adding to the patient report information related to the proportion of the total time period for the first day not spent in cardiac arrhythmia. Adding to the patient report information can include adding information related to a chart including: a graph, including a first axis representing time and a second axis representing date; a bar on the graph having a dimension parallel to the first axis wherein the length of the dimension depicts the total time period of monitoring for the first day; a first color on the bar and a second color on the bar; wherein the amount of the first color with respect to the second color is proportional to the proportion of the total time period for the first day spent in cardiac arrhythmia; and wherein the amount of the second color with respect to the first color is proportional to the proportion of the total time period for the first day not spent in cardiac arrhythmia.

The computer-readable storage device can be further operable to cause the one or more computers to perform operations including: calculating from the obtained data a maximum, a minimum, and an average heart rate for the proportion of the total time period for the first day spent in cardiac arrhythmia; calculating from the obtained data a maximum, a minimum, and an average heart rate for the proportion of the total time period for the first day not spent in cardiac arrhythmia; and wherein adding to the patient report information can include adding information related to: the maximum, the minimum, and the average heart rate calculated for the proportion of the total time period spent in cardiac arrhythmia; and the maximum, the minimum, and the average heart rate calculated for the proportion of the total time period not spent in cardiac arrhythmia. Adding to the patient report information can include adding information related to a chart including: a graph, including a first axis representing heart rate and a second axis representing date of monitoring; a first bar on the graph having a dimension parallel to the first axis; the first bar having a first end proximal to the second axis and a second end distal to the second axis, wherein the first end represents the minimum heart rate and the second end represents the maximum heart calculated for the proportion of the total time period spent in cardiac arrhythmia; a first indicator on the first bar for indicating the average heart rate calculated for the proportion of the total time period spent in cardiac arrhythmia; a second bar on the graph having a dimension parallel to the first axis; the second bar having a first end proximal to the second axis and a second end distal to the second axis, wherein the first end represents the minimum heart rate and the second end represents the maximum heart calculated for the proportion of the total time period not spent in cardiac arrhythmia; and a second indicator on the second bar for indicating the average heart rate calculated for the proportion of the total time period not spent in cardiac arrhythmia.

Adding information related to a chart can include adding information related to the first and second indicator wherein the first indicator can have a different color or shape than the second indicator. The computer-readable storage device can be further operable to cause the one or more computers to perform operations including determining a total time period of monitoring for a second or more days; calculating from the obtained data a proportion of the total time period spent in cardiac arrhythmia for each of the second or more days; and wherein adding information to the patient report can include adding information related to: the total time period for each of the second or more days; and the proportion of the total time period spent in cardiac arrhythmia for each of the second or more days. The computer-readable storage device can be further operable to cause the one or more computers to perform operations including calculating from the obtained data a proportion of the total time period not spent in cardiac arrhythmia for each of the second or more days; and wherein adding to the patient report information can include adding information related to the proportion of the total time period not spent in cardiac arrhythmia for each of the second or more days. Obtaining data associated with cardiac arrhythmia events can include obtaining data associated with the on-set and off-set of a cardiac arrhythmia event. The computer-readable storage device can be further operable to cause the one or more computers to perform operations can include receiving human assessment data associated with the cardiac arrhythmia events; and modifying the proportion of the total time period for the first day spent in cardiac arrhythmia based on the human assessment data. The computer-readable storage device can be further operable to cause the one or more computers to perform operations including calculating a longest cardiac arrhythmia episode; and wherein adding to the patient report information can include adding information related to one or more of: the total time monitored; the total time spent in cardiac arrhythmia; the maximum heart rate for the proportion of the total time period spent in cardiac arrhythmia; a longest cardiac arrhythmia episode; the average heart for the proportion of the total time period spent in cardiac arrhythmia; and the average heart rate for the proportion of the total time period not spent in cardiac arrhythmia.

In a third aspect, a machine implemented method includes obtaining data associated with cardiac arrhythmia events and heart rate in a monitored living being; determining a total time period of monitoring for each of a plurality of days; calculating from the obtained data for each of the plurality of days a proportion of the total time period spent in cardiac arrhythmia and a proportion of the total time period not spent in cardiac arrhythmia; generating for display a patient report that includes adding information to a single chart related to: summary statistical data for the proportion of the total time period for the plurality of days spent in cardiac arrhythmia. The method further includes summary statistical data for the proportion of the total time period for the plurality of days not spent in cardiac arrhythmia.

Implementations can include any, all, or none of the following features. Obtaining data associated with cardiac arrhythmia events can include obtaining data associated with atrial fibrillation events; calculating from the obtained data for each of the plurality of days a proportion of the total time period spent in cardiac arrhythmia and a proportion of the total time period not spent in cardiac arrhythmia can include calculating from the obtained data for each of the plurality of days a proportion of the total time period spent in atrial fibrillation and a proportion of the total time period not spent in atrial fibrillation; and adding information to a single chart related to summary statistical data for the proportion of the total time period for each of the plurality of days spent in cardiac arrhythmia comprises adding information to a single chart related to summary statistical data for the proportion of the total time period for each of the plurality of days spent in atrial fibrillation; and adding information to a single chart related to summary statistical data for the proportion of the total time period for each of the plurality of days not spent in cardiac arrhythmia can include adding information to a single chart related to summary statistical data for the proportion of the total time period for each of the plurality of days not spent in atrial fibrillation. Adding information to a single chart can include adding information related to: the total time period of monitoring for each of the plurality of days; wherein the information related to the summary statistical data for the proportion of the total time period for each of the plurality of days spent in cardiac arrhythmia can include a percentage of the total time period for each of the plurality of days spent in cardiac arrhythmia; and wherein the information related to the summary statistical data for the proportion of the total time period for each of the plurality of days not spent in cardiac arrhythmia can include a percentage of the total time period for each of the plurality of days not spent in cardiac arrhythmia. Adding information to a single chart can include adding information related to: a graph, including a first axis representing a duration of time and a second axis representing date; a bar for each of the plurality of days on the graph, each having a dimension parallel to the first axis wherein the length of the dimension depicts the total time period of monitoring for each of the plurality of days; a first color on each bar and a second color on each bar; wherein the amount of the first color with respect to the second color on each bar can be proportional to the proportion of the total time period for the each of the plurality of days spent in cardiac arrhythmia; and wherein the amount of the second color with respect to the first color on each bar can be proportional to the proportion of the total time period for each of the plurality of days not spent in cardiac arrhythmia.

The machine implemented method can include calculating from the obtained data a maximum, a minimum, and an average heart rate for the proportion of the total time period spent in cardiac arrhythmia for each of the plurality of days; calculating from the obtained data a maximum, a minimum, and an average heart rate for the proportion of the total time period not spent in cardiac arrhythmia for each of the plurality of days; and wherein adding information to a single chart can include adding information related to: the maximum, the minimum, and the average heart rate calculated for the proportion of the total time period spent in cardiac arrhythmia for each of the plurality of days; and the maximum, the minimum, and the average heart rate calculated for the proportion of the total time period not spent in cardiac arrhythmia for each of the plurality of days. Adding information to a single chart can include adding information related: a graph, including a first axis representing heart rate and a second axis representing the date of monitoring; a first bar for each of the plurality of days on the graph, each bar having a dimension parallel to the first axis; the each of the first bars having a first end proximal to the second axis and a second end distal to the second axis, wherein the first end represents the minimum heart rate and the second end represents the maximum heart calculated for the proportion of the total time period spent in cardiac arrhythmia for each of the plurality of days; a first indicator on each of the first bars for indicating the average heart rate calculated for the proportion of the total time period spent in cardiac arrhythmia for each of the plurality of days; a second bar for each of the plurality of days on the graph, each having a dimension parallel to the first axis; each of the second bars having a first end proximal to the second axis and a second end distal to the second axis, wherein the first end represents the minimum heart rate and the second end represents the maximum heart calculated for the proportion of the total time period not spent in cardiac arrhythmia for each of the plurality of days; and a second indicator on each of the second bars for indicating the average heart rate calculated for the proportion of the total time period not spent in cardiac arrhythmia for each of the plurality of days. Adding information related to a graph can include adding information relating the first indicators, the first indicators having a consistent color or shape different from the second indicators.

In a fourth aspect, a system includes a monitoring device configured to obtain physiological data for a living being and to generate annotation data based on the physiological data for a total time period; a processing system configured to obtain the annotation data via a communication channel from the monitoring device and to generate for display based on the annotation data a daily patient report that includes, a chart showing summary statistical data for a proportion of a total monitored time period spent in cardiac arrhythmia for a plurality of days and summary statistical data for a proportion of the total monitored time period not spent in cardiac arrhythmia for the plurality of days.

Implementations can include any, all, or none of the following features. Cardiac arrhythmia can include atrial fibrillation. The processing system can be further configured to receive a request for the physiological data and to obtain the physiological data from the monitoring device. The physiological data can include ECG data and heart rate data. The processing system can be configured to receive alterations in the annotation data. The summary statistical data can include for each of the plurality of days: the total monitored time, a percentage of the total monitored time spent in cardiac arrhythmia, and a percentage of the total monitored time not spent in cardiac arrhythmia. The summary statistical data can include for each of the plurality of days: a minimum heart rate, a maximum heart rate, an average heart rate for the proportion of the total monitored time spent in cardiac arrhythmia, and a minimum heart rate, a maximum heart rate, an average heart rate for the proportion of the total monitored time not spent in cardiac arrhythmia.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 3-4 show an example daily patient report.

FIG. 5 shows another example daily patient report.

FIGS. 6-7 show an example end of service summary report.

Like reference symbols in the various drawings indicate like elements.

DETAILED DESCRIPTION

Figure 1:
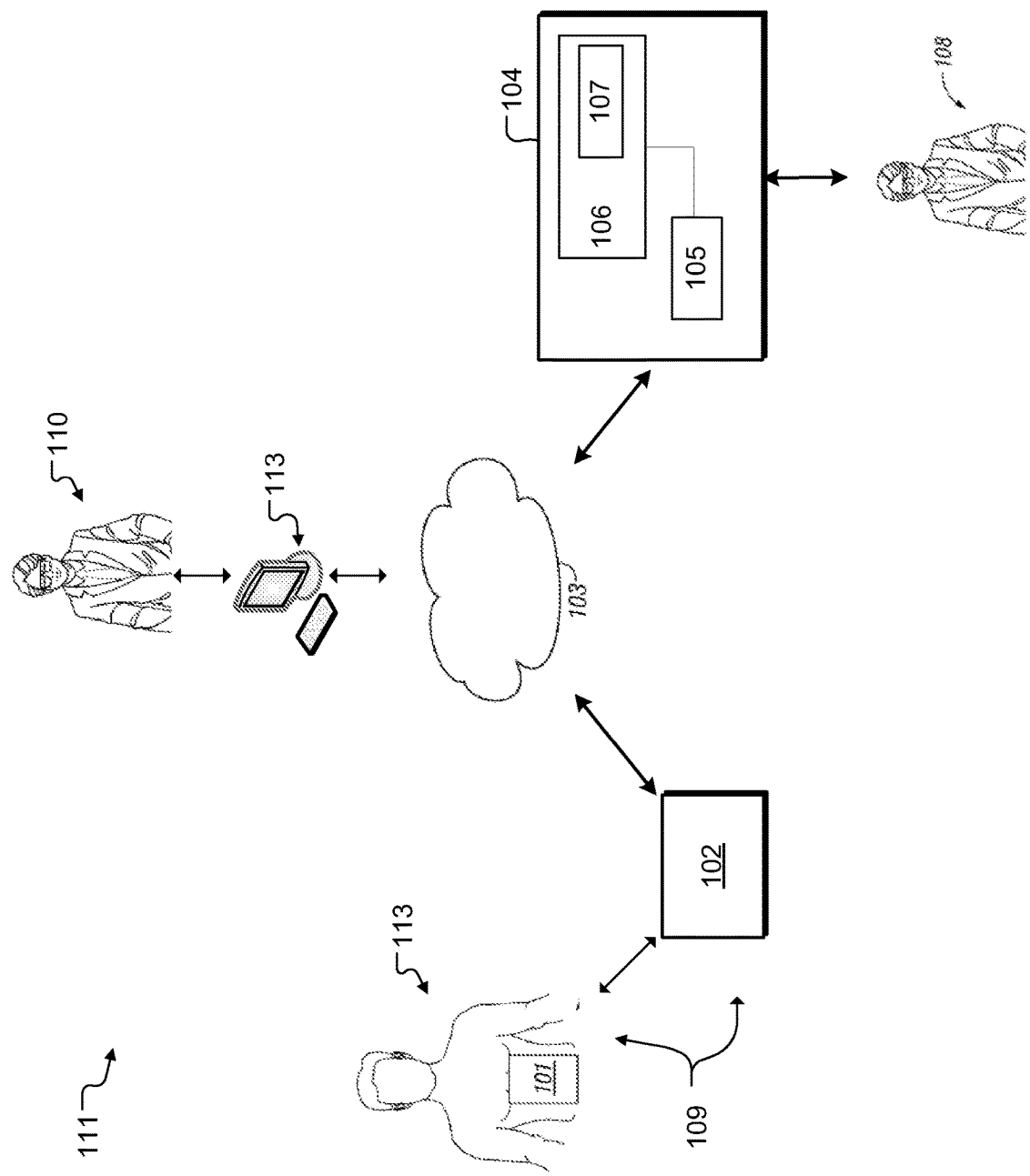
FIG. 1 shows an example system for reporting information related to arrhythmia events.

FIG. 1 shows an example system 111 for reporting information related to cardiac arrhythmia events, such as atrial fibrillation (AF) events. A monitoring system 109 can communicate (via devices 101 and 102) ECG (electrocardiogram), cardiac event, heart rate data, and other data to monitoring center 104. The monitoring system 109 can include, for example, an implantable medical device (IMD), such as an implantable cardiac defibrillator and an associated transceiver, or a pacemaker and an associated transceiver, or a monitoring device 101 that a patient 113 wears. Further, monitoring system 109 can include a monitor processing device 102 that can send physiological data (received from monitoring device 101) to monitoring center 104 and that can detect arrhythmia events (such as atrial fibrillation events). In some implementations, the devices 101 and 102 are integrated into a single device. Moreover, the system 109 can be implemented using, for example, the CardioNet Mobile Cardiac Outpatient Telemetry (MCOT) device, which is commercially available and provided by CardioNet, Inc. of San Diego, Calif.

Monitor processing device 102 can transmit physiological data (including data related to arrhythmia events) through a communication network 103, which can be a local area network (LAN), a landline telephone network, a wireless network, a cellular network, a satellite communication network, or other suitable network to facilitate two-way communication with monitoring center 104. Advantageously, monitoring center 104 can be located in the same location (e.g., in the same room or building) as monitoring system 109 or at some remote location.

The monitoring center 104 can include a monitoring (or display) station 105 and a processing system 106. The processing system 106 can include one or more storage devices 107, such as a mass storage device or a volatile memory device. A health care provider 108, such as a cardiovascular technician (CVT), can use the monitoring station 105 to evaluate physiological data received from monitoring system 109. In some implementations, the health care provider 108 can identify and report, among other things, arrhythmia events (such as atrial fibrillation events). The health care provider 108 can report these assessments by annotating the physiological data and providing the annotation data to the processing system 106. Annotation data can include data such as the type of arrhythmia events; the start and end time of arrhythmia events; maximum heart rate; minimum heart rate; average heart rate; statistical standard deviation of heart rate recorded during arrhythmia events; and data that describes morphology, and/or intervals, such as QRS duration, QT duration, or PR duration during arrhythmia events. In some implementations, monitoring system 109 can identify arrhythmia events and generate annotation data associated with those events. The monitoring system 109 communicates the annotation data to the monitoring center 104 via network 103. In some examples, the monitoring system 109 can communicate the annotation data to monitoring center 104 without the ECG data.

Based on the annotation data, the monitoring center 104 can generate a report, such as a summary report related to both arrhythmia and heart rate data. The summary report generated by the processing system 106 based on the annotation data can include a daily patient report. In some implementations, the monitoring system 109 can generate a summary report such as a daily patient report. The summary report can be displayed by monitoring station 105 to a health care provider 108 such as a CVT, a nurse, or a physician, who has access to the monitoring station 105. Based on the health care provider's review, the health care provider 108 can request more information from the monitoring system 109, such as ECG data stored in the monitoring system. After reviewing the ECG data, the health care provider 108 can identify errors in the annotation data, such as improperly identified arrhythmia events or arrhythmia events that were not identified. If the health care provider 108 changes, modifies, and/or rejects the annotation data, the report also changes accordingly.

The processing system 106 also can provide a report related to both arrhythmia and heart rate data to a health care provider 110, such as a doctor, via network 103 or other such network. The health care provider 110 can obtain the report using a computer 113 connected to the network 103. The computer 113, can include, for example, any processing device that can access the network 103 such as a PDA, cell phone, or the like. In other examples, the health care provider 110 can receive the report using a facsimile.

Figure 2:
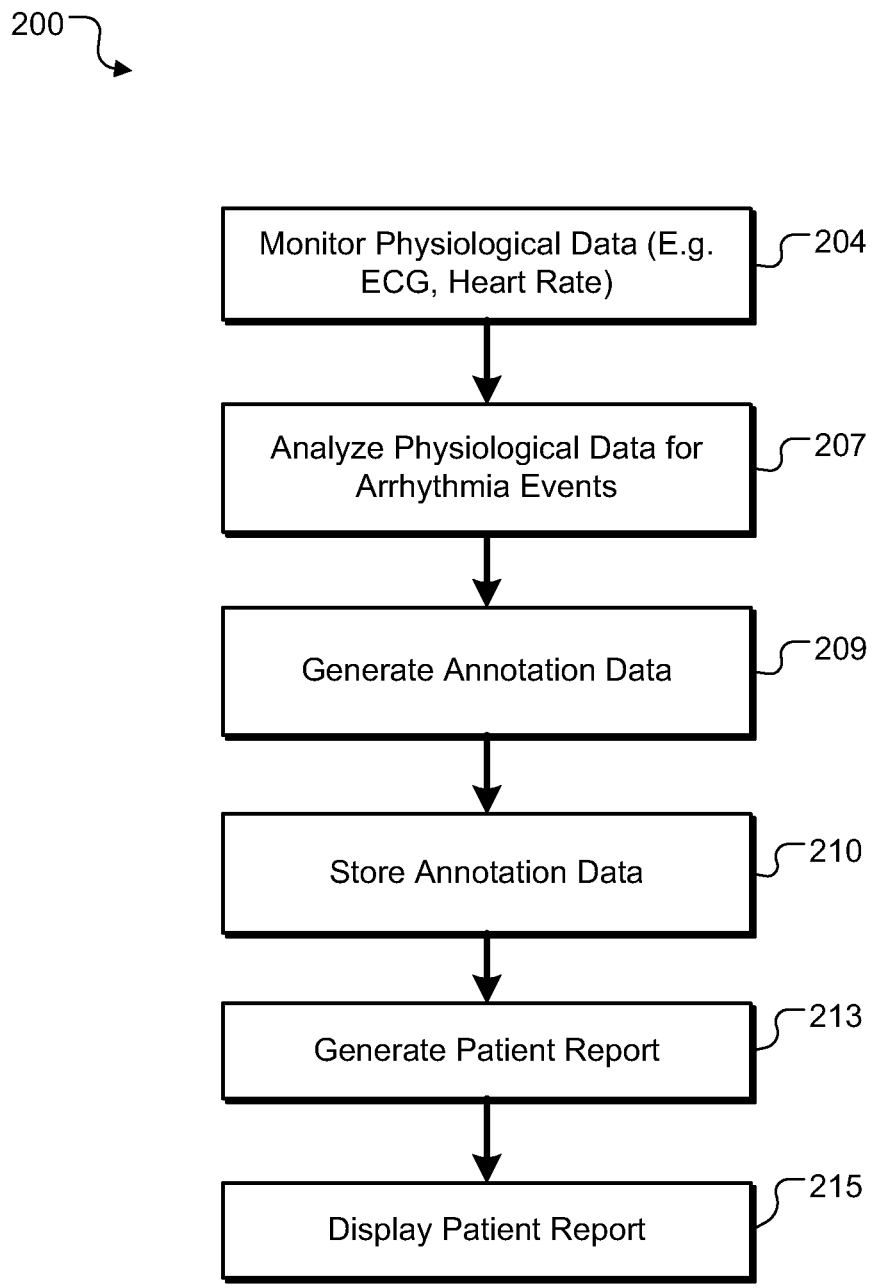
FIG. 2. shows an example procedure for monitoring, processing, and reporting arrhythmia event data in a daily patient report.

FIG. 2. shows an example procedure 200 for monitoring, processing, and reporting arrhythmia event data in a daily patient report. At 204, physiological data is monitored. For example, monitoring system 109 (illustrated in FIG. 1) monitors physiological data, such as ECG data and heart rate data. At 207, various parts of this physiological data can be analyzed and arrhythmia events can be identified based on predefined criteria (e.g. RR variability and QRS morphology). At 209, annotation data is generated based on the analyzed physiological data. The analysis and annotation data generation can be performed, for example, by the monitoring system 109. The monitoring system 109 can analyze the physiological data for arrhythmia events, annotate the physiological data accordingly, and report the annotated data to the processing system at 106. In another example, the monitoring system 109 reports physiological data to the processing system 106, and the processing system 106 analyzes and annotates the physiological data. Further, a health care provider can analyze various parts of the physiological data received from monitoring system 109 and identify arrhythmia events. The health care provider also can adjust arrhythmia events incorrectly identified by either the monitoring system 109 or the processing system 106.

At 210, the annotation data associated with the analyzed physiological data is stored. The data can be stored, for example, at the monitoring system 109, the monitoring center 104, or in remote storage device via network 103. At 213, process 200 generates a patient report, such as a daily patient report, based on the stored data. The daily patient report can be generated upon request by a health care provider or can be generated automatically at a specified time each day the patient is monitored. The daily patient report can include summary data for each day that the patient has been monitored in a monitoring cycle. In some implementations, a daily patient report can be generated on a real-time basis. For example, a daily patient report can display summary data from previous days and can display a cumulative summary data for the present day that is updated on a real-time basis. At 215, the patient report can be displayed by monitoring station 105. In other examples, the patient report can be displayed via network 103 to a remote health care provider at 113.

Figure 4:
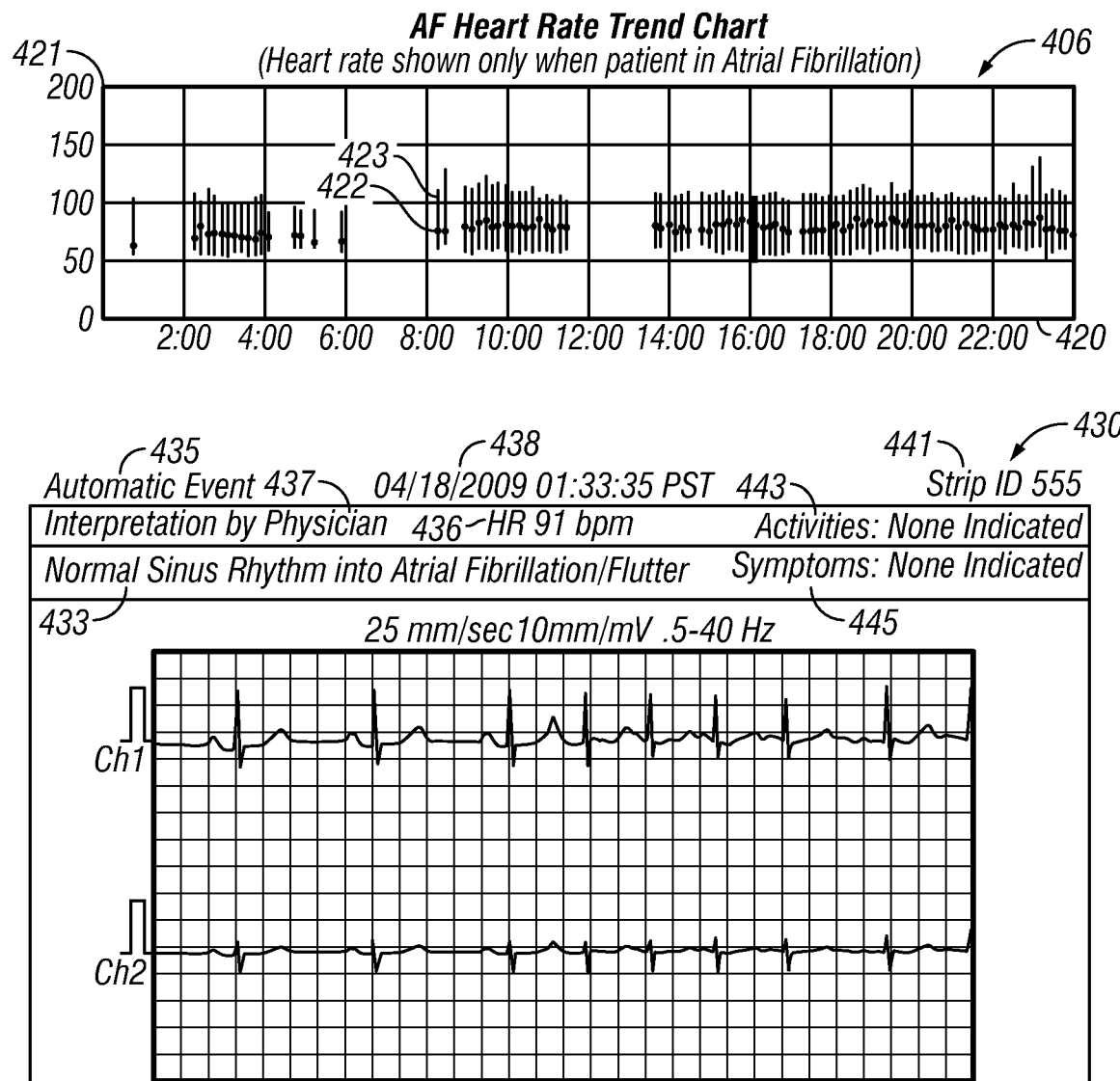

FIGS. 3-4 show an example daily patient report 302. In FIG. 3, the daily patient report 302 can include a report identification (ID) 305 for identification of the report. The daily patient report also can include a patient data table 308, which includes patient information for a patient being monitored, such as name, date of birth, gender, patient phone number, ID number such as a social security number, and the patients medical record number. The patient data table 308 also includes information regarding the prescribing physician and referring physician at 311.

The patient report also can include the date 314 when the patient was monitored. If the patient has undergone an ablation treatment, the date of ablation can be included, for example at 312. The patient report can include information regarding the patients monitoring schedule. For example, at 315 the patient report shows when the patient is scheduled for monitoring following the ablation procedure indicated at 312. In this particular example, the patient is scheduled for monitoring 3 months after the ablation indicated at 312 and 9 months after the ablation indicated at 312. In some examples, an actual date can be used to show when the patient is scheduled for ablation monitoring. The patient report can also include the patients diagnosis. For example, at 317 the patient diagnosis is indicated with an International Classification of Disease Code ("ICD").

The daily patient report 302 also includes a heart rate trend chart 318 for pictographically presenting both heart rate trend and atrial fibrillation burden on a common time scale (to "pictographically present" such data, however, a graph is not required). The term "atrial fibrillation burden" (or more generally, "arrhythmia event burden") refers generally to the overall amount of time that a patient is in atrial fibrillation (or arrhythmia) over a specified time period, taking into account the number and duration of episodes. The heart rate trend chart 318 has a time axis 320 that represents time of day and a heart rate axis 321 that represents heart rate in beats per minute. For the heart rate trend chart 318, heart rate data and atrial fibrillation data is divided into ten minute segments. A line 323 with a dot 322 is graphed along the time axis 320 for each monitored ten minute segment. The location of the line 323 with respect to the time axis 320 indicates the time of day during which the ten minute segment occurred. For durations when no monitoring occurred, for example time segment 326, there are no lines and no dots. The line 323 is parallel to the heart rate axis 321. The location of the top of the line with respect to the heart rate axis 321 indicates the maximum detected heart rate during the respective ten minute segment. The location of the bottom of the line with respect to the heart rate axis 321 indicates the minimum detected heart rate during the respective ten minute segment. In other implementations, the location of the top of the line and the bottom of the line with respect to the heart rate axis 321 can indicate the statistical standard deviation of the heart rate during the respective ten minute segment. The location of dot 322 on the line 323 with respect to the heart rate axis 321 indicates the average heart rate measured for the respective ten minute segment.

Monitoring system 109 also transmits a "flag" if it detects one or more atrial fibrillation (AF) events. These flags are graphed on the heart rate trend chart 318 in blocks 324 along the time axis 320 at the location where that flag occurred during the day. The resolution of the segments can vary. In the example shown in FIG. 3, atrial fibrillation events lasting less than ten minutes on the graph are graphed as ten minute segments whereas the AF events only require 30 seconds to detect. In other implementations, the blocks 324, lines 323 and dots 322 can be detected and graphed in higher resolution. In some examples, the resolution can be based on the time period it takes to detect an atrial fibrillation event, such as 30 seconds, 10 seconds, etc. Also, in some examples, the heart rate trend chart can be zoomed-in on to show higher resolution. For example, the heart rate trend chart can initially show heart rate trend data in ten minute intervals but when a user zooms-in on the chart, higher resolutions can be displayed, such as 30 second or 20 second intervals, etc. The atrial fibrillation events can be detected using various algorithms, such as algorithms that use RR variability or P-wave presence.

The daily patient report 302 also includes a daily AF burden chart 327. The AF burden chart 327 contains information relating to the total monitored time (the duration of time that the patient was monitored in a day), the proportion of the total monitored time spent in atrial fibrillation, and the proportion of the total monitored time not spent in atrial fibrillation. In some examples, the time not spent in atrial fibrillation can include other types of arrhythmias such as normal sinus arrhythmia. Also in some examples, the total time spent in atrial fibrillation (or in arrhythmia events) can include only usable data.

In the example shown in FIG. 3, the AF burden chart 327 is shown as a graph having a date axis 329 that represents the date of monitoring and a time axis 330 that represents duration of time. The date indicated, for example, is Apr. 18, 2009—the date the patient was monitored. The AF burden chart has a bar 332 on the graph, the bar having a dimension parallel the to time axis 330. In the example shown, the dimension is vertical. The length 338 of the vertical dimension of bar 332 with respect to time axis 330 indicates the total monitored time period for the date the patient was monitored. The bar 332 has a first color 334 and a second color 336. As shown by the key 333, the first color 334 indicates the proportion of the total monitored time spent in atrial fibrillation, and the second color 336 indicates the proportion of the total monitored time not spent in atrial fibrillation. The amount of the first color 334 with respect to the second color 336 is proportional to the percentage of the total monitored time spent in atrial fibrillation. In like manner, the amount of the second color 336 with respect to the first color 334 is proportional to the percentage of the total monitored time not spent in atrial fibrillation. In the example shown, for the date Apr. 18, 2009, the first color 334 is 42% of the bar 332 whereas the second color 336 is 58% of the bar 332. Accordingly, the time spent in atrial fibrillation in this example on Apr. 18, 2009 is 42 percent of the total monitored time period.

Unlike the heart rate trend chart 318 shown in FIG. 3, the daily AF burden chart 327 shows summary data for the actual amount of time the patient was detected in atrial fibrillation and the actual amount of time the patient was detected not in atrial fibrillation for the total monitored time. The heart rate trend chart 318 shows the AF burden in ten minute blocks 324, and therefore the total AF burden shown on the heart rate trend chart 318 tends to be greater than the actual detected AF burden. For example, if only one AF event occurred in a ten minute segment and if the duration of that AF event occurred for less than ten minutes, that particular AF event is shown (depending upon the resolution) on the heart rate trend chart 318 as a ten minute segment. On the other hand, the daily AF burden chart shows a summary of the actual AF burden for the total monitored time for the day.

The daily patient report 302 also includes a daily average heart rate (HR) chart 340. The daily average HR chart contains information relating to (1) the average heart rate, maximum heart rate, and minimum heart rate for the proportion of the total monitored time spent in atrial fibrillation, and (2) the average heart rate, maximum heart rate, and minimum heart rate for the proportion of the total monitored time period not spent in atrial fibrillation. The daily average HR chart 340 is shown as a graph having a date axis 342 that represents the date of monitoring and a heart rate axis 343 that represents heart rate in beats per minute (bpm). The date indicated here, for example, is Apr. 18, 2009—the date the patient was monitored.

The daily average heart rate (HR) chart 340 has a first bar 349 showing summary data for the proportion of total monitored time period spent in atrial fibrillation for the date the patient was monitored as shown on date axis 342. The daily average HR chart also has a second bar 346 showing summary data for the proportion of the total monitored time period not spent in atrial fibrillation for the date the patient was monitored. The first bar 349 and the second bar 346 each has a dimension parallel to heart rate axis 343. In this case, the dimension of each bar is vertical and the bar is in the form of line. The first bar 349 has an indicator 352, a top 350, and a bottom 354. The indicator 352 is in the shape of square and has a first color. As shown by key 355, the color and/or shape of the first indicator 352 indicates that the bar 349 is representative of summary data for the proportion of the total monitored time spent in atrial fibrillation for the date the patient was monitored. The first indicator 352, for example, indicates the average heart rate for the proportion of the total monitored time spent in atrial fibrillation based on the location of the first indicator 352 with respect to the heart rate axis 343. Based on their locations with respect to the heart rate axis 343, the top 350 of the first bar 349 shows the maximum heart rate and the bottom 354 shows the minimum heart rate for the proportion of the total monitored time period spent in atrial fibrillation for the date the patient was monitored. In other implementations, the top 350 and the bottom 354 of the first bar 349 can show the statistical standard deviation of heart rate for the proportion of the total monitored time period spent in atrial fibrillation for the date the patient was monitored.

The second bar 346 has and indicator 347, a top 344, and a bottom 348. The indicator 347 of the second bar 346 has a shape and a second color different from the shape and color of the first indicator 352 of the first bar 349. As shown by key 355, the color and/or shape (diamond shape) of the second indicator 347 indicates that the second bar 346 shows summary data for the proportion of the total monitored time period not spent in atrial fibrillation for the date the patient was monitored. The second indicator 347, for example, indicates the average heart rate for the proportion of the total monitored time not spent in atrial fibrillation based on the location of the second indicator 347 with respect to the heart rate axis 343. Based on their locations with respect to the heart rate axis 343, the top 344 of the second bar 346 shows the maximum heart rate and the bottom 348 shows the minimum heart rate for the proportion of the total monitored time period not spent in atrial fibrillation for the date the patient was monitored. In other implementations, the top 344 and the bottom 348 of the second bar 346 can show the statistical standard deviation of heart rate for the proportion of the total monitored time period not spent in atrial fibrillation for the date the patient was monitored.

In some implementations, the color used in the daily patient report that shows data for the time spent in atrial fibrillation is consistent throughout daily patient report. In like manner, the color used in the daily patient report that shows data for the monitored time not spent in atrial fibrillation is consistent throughout the daily patient report.

The daily patient report also includes an atrial fibrillation (AF) statistics table 360 for the date the patient was monitored. The statistics table includes summary data for the date the patient was monitored, such as the total time monitored, the time spent in AF, the highest heart rate in AF, the time the highest heart rate in AF was recorded, the duration of longest AF episode, the time the longest AF episode began, the average heart rate during the proportion of monitored time spent in AF, and the average heart rate during the proportion of monitored time not spent in AF.

FIG. 4 shows more data that can be included in the daily patient report 302. The data in FIG. 4 can be included together with the data shown in FIG. 3, for example, on the same page. In other examples, the data in patient report 302 can be included on a multiple pages. FIG. 4 includes an AF heart rate trend chart 406 for pictographically presenting heart rate trend data only for segments of time during which the patient was in atrial fibrillation. The heart rate trend chart 406 has a time axis 420 that represents the time of day and a heart rate axis 421 that represents heart rate in beats per minute. In the example shown, the AF heart rate trend data is reported in ten minute segments. A line 423 with a dot 422 is graphed along the time axis 420 for each monitored ten minute segment where the patient experienced an atrial fibrillation event. For durations when no monitoring occurred or when no atrial fibrillation event was detected, there is no line 423 and no dot 422. The line 423 indicates the range of detected heart rates for a given ten minute segment. The location of the top of the line with respect to the heart rate axis 421 indicates the maximum detected heart rate during the respective ten minute segment. The location of the bottom of the line with respect to the heart rate axis 421 indicates the minimum detected heart rate during the respective ten minute segment. In other implementations, the location of the top of the line and the bottom of the line with respect to the heart rate axis 421 can indicate the statistical standard deviation of the heart rate during the respective ten minute segment. The location of the dot 422 with respect to the heart rate axis 421 indicates the average heart rate measured for the respective ten minute segment. In other implementations, lines 423 and dots 422 can be graphed in higher resolution, such as every 30 seconds, 20 seconds, or 10 seconds. In some examples, a heart rate trend chart such as heart rate trend chart 318 or heart rate trend chart 406 can be displayed on each page of a daily patient report.

The daily patient report also can include an ECG chart 430. The ECG chart 430 has a graph of a portion of the ECG data for the day the patient was monitored. The portion provided can be selected as a representative of the primary type of AF events the patient experienced during the day. In other examples, the portion provided can be an AF event of particular interest. The ECG chart 430 can also show how the portion of the ECG data was selected at 315. In this example, the "automatic event" 435 indicates that data for an AF Event was generated automatically, for example, by the monitoring center 104 or monitoring system 109. In other examples, the portion of the ECG data can be selected by a health care professional such as a technician monitoring the data. In other examples, the portion of the ECG data can be selected by the patient, such as when the patient identifies to the monitoring system 109 that he or she is experiencing an abnormal event like an AF Event.

At 437, the daily patient report can include information on who provided the diagnosis which is shown at 433, which indicates, in this example, that the detected AF Event shown by the ECG data is diagnosed as "Normal Sinus Rhythm into Atrial Fibrillation/Flutter." The ECG chart also has a date and time stamp 438 indicating the start time of the ECG data, and the heart rate 436 calculated during the atrial fibrillation event. Also, the ECG chart has a strip ID 441 for identifying the record containing the ECG data. Also, the ECG chart has an activity field 443 that indicates what activity the patient was participating in when the AF Event shown by the ECG chart occurred. The ECG also includes a symptom field 445 for indicating symptoms the patient was experiencing when the AF Event shown by the ECG chart occurred.

The daily patient report 302 also includes an interpretation field 448 where a physician can provide his or her interpretation of the information provided in the daily patient report 302. In this example, the physician's interpretation is "intermittent atrial fibrillation with normal sinus beats."

FIG. 5 shows another example of a daily patient report. The daily patient report 502 includes summary data for multiple days. In this example, the days are consecutive days. A daily patient report can include summary data for any number of days. In some embodiments, the patient report can include summary data for all of the days a patient has been monitored during a monitoring service period. A doctor can prescribe, for example, that a patient be monitored for a service period of twenty-one days. Each day the patient is monitored, a daily patient report can be generated that includes summary data for each day the patient has been monitored during the service period.

The daily patient report 502 includes patient ID table 508 with data as described in connection with FIG. 3. The daily patient report 502 includes a date 514. In some examples, the date 514 can be the most recent date for which the patient report contains summary data. In some examples, the patient report 502 can include summary data for the most recent date of monitoring. The daily patient report 502 also includes heart rate trend chart 518. The heart rate trend chart 518 pictographically presents, as described in connection with FIG. 3, both heart rate trend and atrial fibrillation burden on a common time scale. In some examples, the heart rate trend chart can be shown for the most recent date of monitoring. In other example, the heart rate trend chart can be shown for a date selected, for example, by a user such as a doctor or other health care professional.

The daily patient report 502 also includes a daily AF burden chart 527. This chart is similar to the AF burden chart 327 described in connection with FIG. 3, except that it shows the summary data for multiple days instead of one. This example shows summary data for five consecutive days, but an AF burden chart can show summary data for any number of days. The AF burden chart 527 contains information relating to the total time period the patient was monitored each day, the proportion of total monitored time for each day spent in atrial fibrillation, and the proportion of total monitored time for each day not spent in atrial fibrillation. In the example shown in FIG. 5, the AF burden chart 527 is shown as a graph having a date axis 529 and a time axis 530. The AF burden chart has five bars 532a, 532b, 532c, 532d, and 532e on the graph, each having a dimension parallel to time axis 530. In this case, the dimension is vertical. The location of each bar along the date axis 529 indicates for which date the bar contains summary data. The height of the vertical dimension of each bar with respect to the time axis indicates the total time the patient was monitored for each day. Each bar has a first color and second color (see e.g. first color 534 and a second color 536). As shown by the key 533, the amount of the first color in each bar indicates the proportion of the total monitored time spent in atrial fibrillation for each day, and the amount of the second color in each bar indicates the proportion of the total monitored time not spent in atrial fibrillation for each day.

The daily patient report 502 also includes a daily average heart rate (HR) chart 540. The daily average HR chart 540 is similar to the daily average heart rate chart 340 discussed in connection with FIG. 3, except that the daily average HR chart 540 has summary data for five days instead of one. It is understood that a daily average HR chart can include summary data for any number of days. The daily average HR chart 540 contains information relating to (1) the average heart rate, maximum heart rate, and minimum heart rate for the proportion of the total monitored time spent in atrial fibrillation for each day, and (2) the average heart rate, maximum heart rate, and minimum heart rate for the proportion of the total monitored time period not spent in atrial fibrillation for each day. In the example shown in FIG. 5, the daily average HR chart 540 is shown as a graph having a date axis and a heart rate axis 543.

The daily average heart rate (HR) chart 540 has five first bars 549a, 549b, 549c, 549d, and 549e. Each of these first bars 549a-e shows summary data for the proportion of the total monitored time period spent in atrial fibrillation for each day the patient was monitored. The daily average HR chart also has five second bars 546a, 546b, 546c, 546d, and 546e. Each of the second bars 546a-e shows summary data for the proportion of the total monitored time period not spent in atrial fibrillation for each day the patient was monitored. The location of each of the bars 549a-e and 546a-e with respect to the date axis 542 indicates for which date each bar contains summary data.

Each of the first bars 549a-e has an indicator, a top, and a bottom. The indicators for the first bars 549a-e are in the shape of square and have a consistent first color. As shown by key 555, the color and shape of the first indicators indicate that bars 549a-e show summary data for the proportion of the total monitored time period spent in atrial fibrillation for each of the five days the patient was monitored. The location of each of the indicators for the first bars 549a-e with respect to the heart rate axis 543 indicates the average heart rate for the proportion of the total monitored time spent in atrial fibrillation for each day. Based on their locations with respect to the heart rate axis 543, each top of the first bars 549a-e shows the maximum heart rate and each bottom shows the minimum heart rate for the proportion of the total monitored time period spent in atrial fibrillation for each day the patient was monitored. In other implementations, the top and bottom of each of the first bars 549a-e can show the statistical standard deviation for the proportion of the total monitored time period spent in atrial fibrillation for each day the patient was monitored.

Each of the second bars 546*a-e* has an indicator, a top, and a bottom. The indicators of the second bars 546*a-e* have a shape and a color different from the shape and color of the indicators of the first bars 549*a-e*. As shown by key 555, the color and shape (diamond shape) of the indicators of the second bars 546*a-e* indicates that the bars 546*a-e* show summary data for the proportion of the total monitored time period not spend in atrial fibrillation for the dates the patient was monitored. The location with respect to the heat rate axis 543 of each of the indicators of the second bars 546*a-e* indicates the average heart rate for the proportion of the total monitored time not spent in atrial fibrillation for each day. Based on their locations with respect to the heart rate axis 543, the top of each of the second bars 546*a-e* indicates the maximum heart rate and the bottom of each of the second bars 546*a-e* shows the minimum heart rate for the proportion of the total monitored time period not spent in atrial fibrillation for each of the days the patient was monitored. In other implementations, the top and bottom of each of the second bars 546*a-e* can show the statistical standard deviation for the proportion of the total monitored time period not spent in atrial fibrillation for each day the patient was monitored.

The daily patient report 502 also includes an atrial fibrillation (AF) statistics table 560, similar to the AF statistics table described in connection with FIG. 3. The AF statistics table 560 can contain statistics for the most recent date the patient was monitored. In other examples, the statistics can be shown for other days, for example, a day selected by a user such as a doctor or other health care professional. The daily patient report 502 also can include an AF heart rate trend chart, ECG chart, and an interpretation field (not shown), as described in connection with FIG. 3. The AF hearth rate trend chart and the ECG chart in patient report 502 can include data for the most recent date of monitoring.

In a situation where a patient is being monitored for multiple days a daily patient report can be generated each day. As in FIG. 5, the daily patient report includes summary data for the each of the previous days the patient was monitored. Based on the daily patient report, the doctor or other health care provider can look for trends and patterns, such as differences in average heart rate between time periods when the patient experienced AF events and when the patient did not experience AF events. Identifying trends and patterns, can help determine the best treatment for a patient. In other examples, a health care provider can look for trends in how much AF burden a patient is experiencing over time. This can be helpful, for example, to determine the success of the last ablation and whether the patient needs further treatment. This can also be helpful, for example, to monitor the trends of patient daily arrhythmia (e.g., atrial fibrillation) burden increase, decrease, or lack of change and to determine the causes associated with such change.

FIGS. 6 and 7 show an example end of service summary report 602. As seen in FIG. 6, the end of service summary report 602 can include a patient data table 608 with identification data for the patient and physician. The end of service summary report 602 also includes summary data for each day of a service period. A service period is a period during which a patient is monitored. The end of service report 602 includes a daily AF burden chart 630. The daily AF burden chart 630 depicts AF burden summary data for each day of the service period, including the total monitored time, the proportion of the total monitored time spent in atrial fibrillation, and the proportion of the total monitored time not spent in atrial fibrillation. The end of service summary report 602 also includes a daily average heart rate chart 640. The daily average heart rate chart 640 depicts heart rate summary data for each day of the service period, including the average, maximum and minimum heart rate for the proportion of time spent in atrial fibrillation, as well as the average, maximum and minimum heart rate for the proportion of time not spent in atrial fibrillation.

The end of service summary report 602 can also optionally include a total service AF Burden chart 650. The total service AF burden chart 650 depicts cumulative AF burden summary data for all of the days of the service period, including the total monitored time for the service period, the proportion of the total monitored time spent in atrial fibrillation for the service period, and the proportion of the total monitored time not spent in atrial fibrillation for the service period. In the example shown in the total service AF burden chart 650, 48% of the total monitored time for the 14 day service period was spend in atrial fibrillation and 52% of the total time was not spent in atrial fibrillation.

The end of service summary report 602 can also include a service summary statistics table 660. The service summary statistics table 660 includes cumulative summary data for all of the days the patient was monitored, such as the total time monitored for the service period, the time spent in AF for the service period, the highest heart rate in AF during the service period, the time the highest heart rate in AF was recorded during the service period, the average heart rate in AF for the service period, and the average heart rate not in AF for the service period.

The end of service summary report 602 also includes a service summary chart 615. The service summary chart 615 includes a emergency reports table 617 that has a list of emergency and/or urgent events reported during the service period, the date the event occurred, symptom or symptoms experience by the patient, the average heart rate during the event, and findings. The findings can include, for example, diagnosis made by a physician, a clinician's findings, or feedback provided by the patient. The service summary chart 615 also includes a daily reports chart 710 as shown in FIG. 7. The daily reports chart 710 can include a list of daily reports with a summary of findings for each of the daily reports and how those findings were obtained. The end of service summary report 602 also includes an interpretation field 725 where a health care provider can record an interpretation of the summary data. The end of service summary report 602 also includes a treatment plan field 735 where a health care profession can prescribe further treatment based on his or her assessment of the daily patient reports and/or the end of service summary report.

Figure 8:
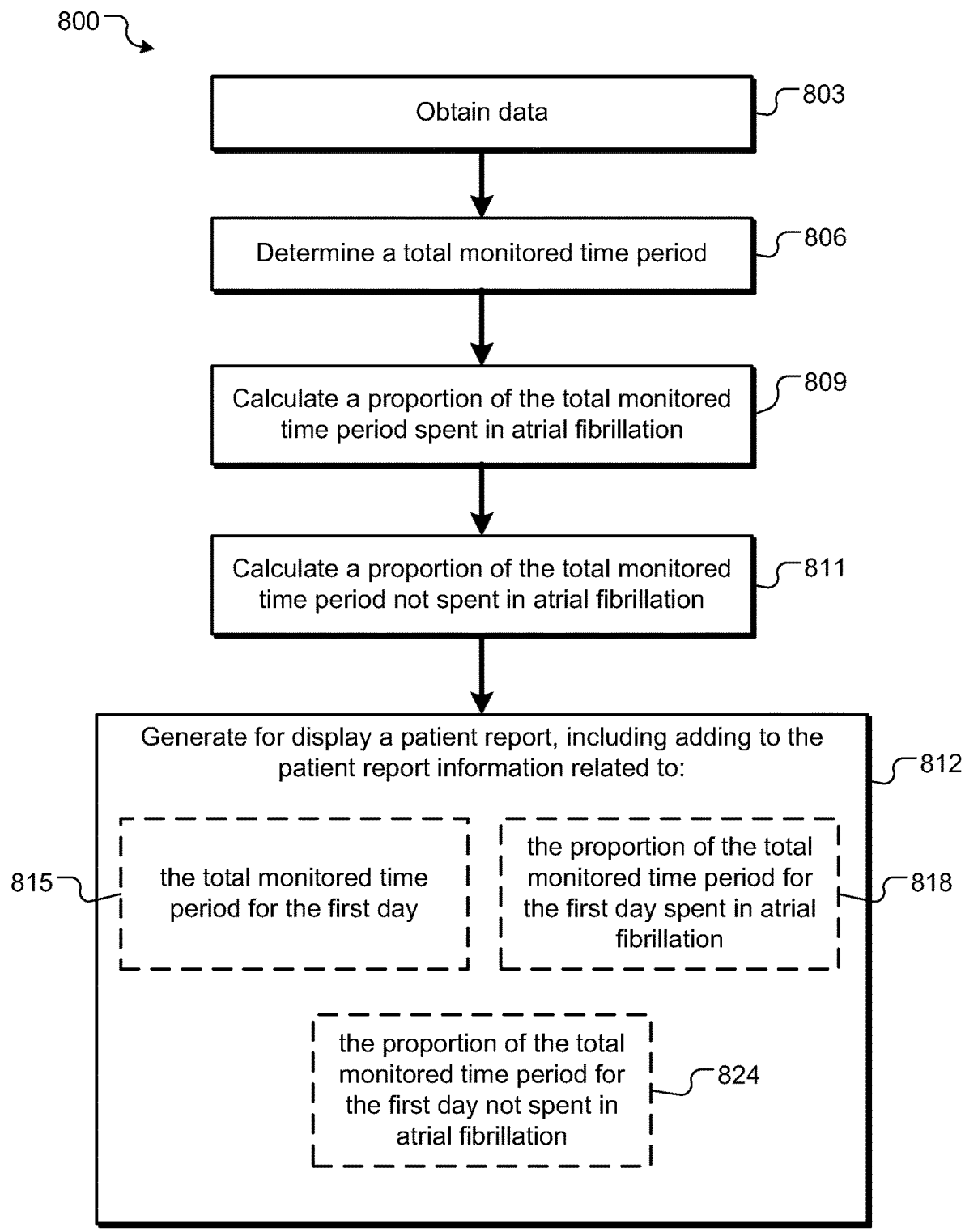
FIG. 8 shows an example process for generating a patient report.

FIG. 8 shows an example process 800 for generating a patient report, such as a daily patient report. At 803, the process 800 obtains data associated with atrial fibrillation and heart rate data for a monitored patient for the day that is the subject of the report. The data can be obtained, for example, from a monitoring system 109 or from a data storage device. At 806, the process 800 determines the total time period during the day for which the patient has been monitored (e.g. the total monitored time period). In some examples, the patient can be monitored for a complete day, in which case the total monitored time would be 24 hours. In other examples, a patient may not be monitored for a complete day. Monitoring can be interrupted for various reasons, for example, if the monitor is temporally disabled, turned-off, or removed. Also, in some examples, the total monitored time can include only the monitored time for which there is usable data, such as data that is not corrupted e.g. by excessive noise.

At 809, the process 800 calculates from the obtained data a proportion of the total monitored time for the day spent in atrial fibrillation. For example, the process 800 can determine what percentage of the total monitored time is spent in atrial fibrillation. Determining what percentage of the total monitored time is spent in atrial fibrillation can include determining that percentage only from usable data. Optionally, at 811 the process 800 can also calculate from the obtained data a proportion of the total monitored time for the day not spent in atrial fibrillation. For example, the process 800 can determine what percentage of the total monitored time is not spent in atrial fibrillation. At 812, the process 800 generates for display a patient report, including adding to the patient report information related to (1) the total monitored time for the first day that the patient was monitored 815, and (2) the proportion of the total monitored time for the first day spent in atrial fibrillation 818. Optionally, at 824, generating for display a patient report can also include adding to the patient report information related to the proportion of the total time period for the first day not spent in atrial fibrillation.

The process 800 can be performed for multiple days. Accordingly, the process 800 can generate for display, for example, a patient report including adding to the patient report information related to the total monitored time for the each of the multiple days, and the proportion of the total monitored time for each day spent in atrial fibrillation.

Figure 9:
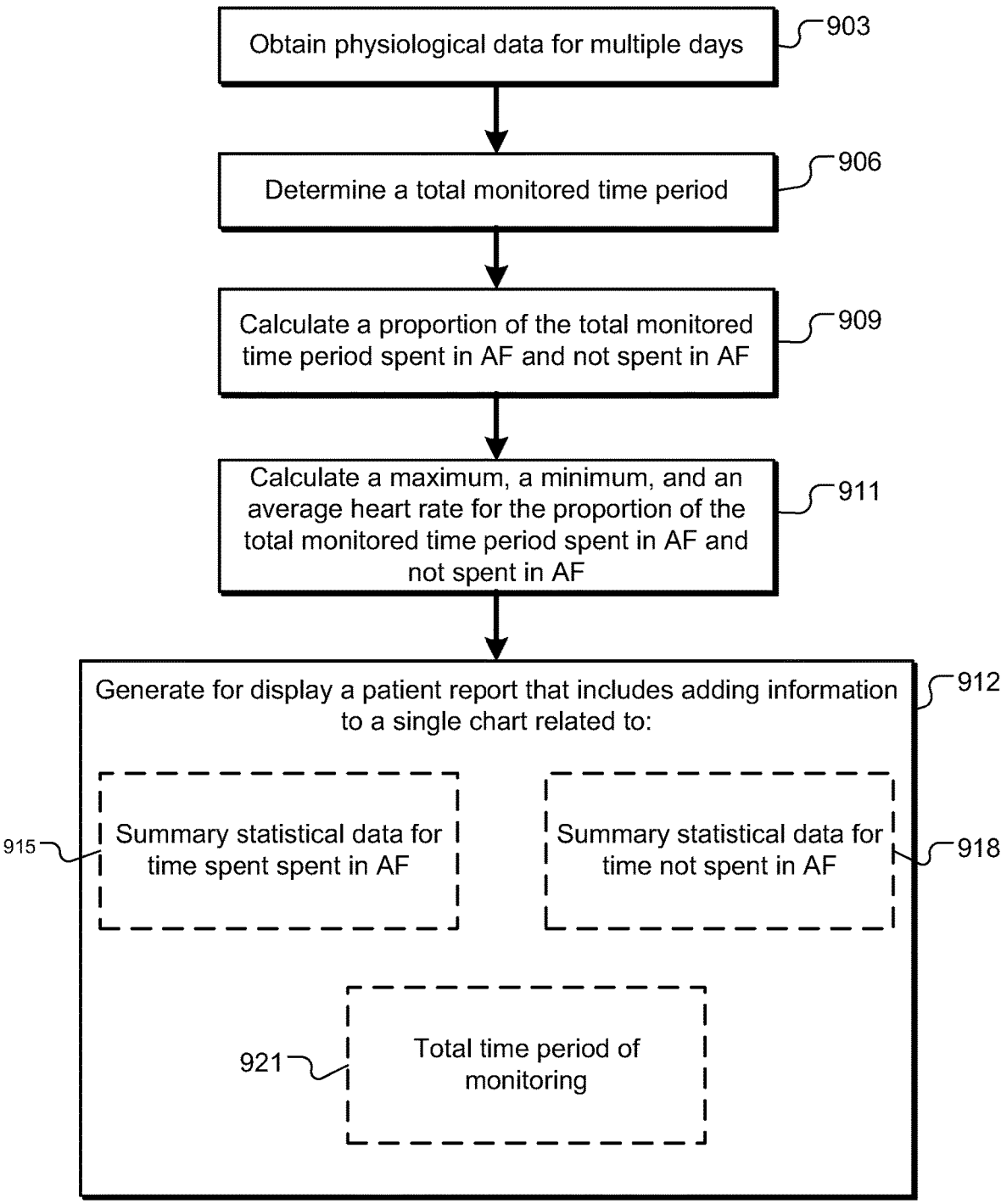
FIG. 9 shows another example process for generating a patient report.

FIG. 9 shows another example process 900 for generating a patient report, such as a daily patient report, for multiple days. At 903, the process 900 obtains physiological data for multiple days, such as data associated with atrial fibrillation events and heart rate data. The data can be obtained, for example, from a monitoring system 109 or from a data storage device. At 906, the process 900 determines a total time period the patient was monitored for each of the multiple of days. At 909, the process calculates from the obtained physiological data a proportion of the total monitored time period spent in atrial fibrillation for each of the days and a proportion of the total monitored time period not spent in atrial fibrillation for each of the days. For each of the days, the process 900 also optionally calculates 911 from the obtained physiological data a maximum, a minimum, and an average heart rate for the proportion of the total time period spent in atrial fibrillation and for the proportion of the total time period not spent in atrial fibrillation. At 912, the process 900 generates for display a patient report that includes adding information to a single chart related to: (1) summary statistical data 915 for the proportion of the total time period for each of the plurality of days spent in atrial fibrillation, and (2) summary statistical data 918 for the proportion of the total time period for each of the plurality of days not spent in atrial fibrillation.

The summary statistical data for the proportion of the total time period for each of the plurality of days spent in atrial fibrillation can also optionally include data related to minimum, maximum, and average HR for the proportion of the total monitored time spent in AF. The summary statistical data for the proportion of the total time period for each of the plurality of days not spent in atrial fibrillation can optionally include data related to minimum, maximum, and average HR for the proportion of the total monitored time not spent in AF.

In some implementations, adding information to a single chart can optionally include adding information related to the total time period of monitoring 921 for each of the plurality of days. The summary data for the proportion of the total time period for each of the plurality of days spent in atrial fibrillation also can include a percentage of the total time period of each of the plurality of days spent in atrial fibrillation. In like manner, the summary data for the proportion of the total time period for each of the plurality of days not spent in atrial fibrillation can include a percentage of the total time period for each of the plurality of days not spent in atrial fibrillation.

The disclosed system and all of the functional operations described and illustrated in this specification can be implemented in digital electronic circuitry, or in computer hardware, firmware, software, or in combinations of the forgoing. Apparatuses can be implemented in a software product (e.g., a computer program product) tangibly embodied in a machine-readable storage device for execution by a programmable processor, and processing operations can be performed by a programmable processor executing a program of instructions to perform functions by operating on input data and generating output. Further, the system can be implemented advantageously in one or more software programs that are executable on a programmable system. This programmable system can include the following: 1) at least one programmable processor coupled to receive data and instructions from, and to transmit data and instructions to, a data storage system; 2) at least one input device; and 3) at least one output device. Moreover, each software program can be implemented in a high-level procedural or object-oriented programming language, or in assembly or machine language if desired; and in any case, the language can be a compiled or an interpreted language.

Also, suitable processors include, by way of example, both general and special purpose microprocessors. Generally, a processor will receive instructions and data from a read-only memory, a random access memory, and/or a machine-readable signal (e.g., a digital signal received through a network connection). The essential elements of a computer are a processor for performing instructions and one or more memory devices for storing instructions and data. Generally, a computer will include one or more mass storage devices for storing data files. Such devices can include magnetic disks, such as internal hard disks and removable disks, magneto-optical disks, and optical disks. Storage devices suitable for tangibly embodying software program instructions and data include all forms of non-volatile memory, including, by way of example, the following: 1) semiconductor memory devices, such as EPROM (electrically programmable read-only memory); EEPROM (electrically erasable programmable read-only memory) and flash memory devices; 2) magnetic disks such as internal hard disks and removable disks; 3) magneto-optical disks; and 4) CD-ROM disks. Any of the foregoing can be supplemented by, or incorporated in, ASICs (application-specific integrated circuits).

To provide for interaction with a user (such as the health care provider), the system can be implemented on a computer system having a display device such as a monitor or LCD (liquid crystal display) screen for displaying information to the user and a keyboard and a pointing device such as a mouse or a trackball by which the user can provide input to the computer system. The computer system can be programmed to provide a graphical user interface through which computer programs interact with users.

A number of embodiments of the invention have been described. Nevertheless, it will be understood that various modifications may be made without departing from the spirit and scope of the invention. For example, the disclosed operations can be performed in a different order and still achieve desirable results. Also, a patient report such as a daily patient report can displayed on paper, instead of on an electronic display device. Also, various examples and embodiments have been described herein for processing and presenting atrial fibrillation information and related data in a patient report. These various examples and embodiments can be used for processing and presenting information related to any type of cardiac arrhythmia such as bradycardias, tachycardias, automaticity, etc. Accordingly, other embodiments are within the scope of the following claims.

What is claimed is:

1. A machine-implemented method comprising:
obtaining ECG data associated with atrial fibrillation events and heart rate in a monitored living being;
determining, from the obtained ECG data, a total time period of monitoring;
calculating a total time period that the monitored living being spent in atrial fibrillation for a first day by integrating atrial fibrillation episodes, taking into account number and duration of the atrial fibrillation episodes, wherein the duration of an atrial fibrillation episode is calculated as time between onset and offset of such atrial fibrillation episode, wherein the time period of monitoring comprises a plurality of contiguous, non-overlapping, equal-length, discrete time intervals, each time interval of the plurality of time intervals having a duration of ten minutes;
flagging each time interval, of the plurality of time intervals, in which an atrial fibrillation event was detected;
calculating from the total time period of monitoring and the total time period that the monitored living being spent in atrial fibrillation for the first day, a percentage of the total time period of monitoring for the first day that the monitored living being spent in atrial fibrillation;
generating, by a computer, for display a patient report, including adding to the patient report information indicating including:
a plurality of blocks, each block representing a particular flagged time interval, and, on a common time scale, average heart rate for each time interval of the plurality of time intervals, whether or not flagged, and wherein a position of each block on the time scale represents a time at which a flagged time interval occurred and wherein a length of each block along the common time scale represents a duration of the flagged time interval represented by the block, and wherein the sum of the durations of the flagged time intervals exceeds the total time period that the living being spent in atrial fibrillation for the first day;
information indicating the total time period of monitoring for the first day; and
a bar graph representing the percentage of the total time period of monitoring for the first day that the monitored living being spent in atrial fibrillation, wherein the bar graph includes a first area having a first appearance, and a second area having a second appearance, wherein the ratio of the first area to the second area is equal to the ratio of the total time period that the living being spent in atrial fibrillation for the first day to the total time period that the living being did not spend in atrial fibrillation for the first day;
information indicating an average heart rate during the total time period that the living being spent in atrial fibrillation for the first day; and
information indicating an average heart rate during the total time period that the living being did not spend in atrial fibrillation for the first day;
selecting a portion of the ECG data corresponding to one of the atrial fibrillation events; and
adding to the patient report a graph of the selected portion of the ECG data.

2. The machine-implemented method of claim 1, further comprising:
calculating, from the total time period of monitoring and the total time period that the monitored living being spent in atrial fibrillation for the first day, a percentage of the total time period of monitoring for the first day that the monitored living being did not spend in atrial fibrillation; and
wherein adding to the patient report information includes adding to the patient report information indicating the percentage of the total time period of monitoring for the first day that the monitored living being did not spend in atrial fibrillation.

3. The machine-implemented method of claim 2, wherein adding to the patient report information includes adding information related to a chart, the information including:
a graph, including a first axis representing a duration of time and a second axis representing date;
a bar on the graph having a dimension parallel to the first axis wherein a length of the dimension depicts the total time period of monitoring for the first day;
a first color on the bar and a second color on the bar;
wherein the amount of the first color with respect to the second color is proportional to the percentage of the total time period of monitoring for the first day that the monitored living being spent in atrial fibrillation; and
wherein the amount of the second color with respect to the first color is proportional to the percentage of the total time period of monitoring for the first day that the monitored living being did not spend in atrial fibrillation.

4. The machine-implemented method of claim 2, further comprising:
calculating from the obtained data a maximum, a minimum, and an average heart rate for the total time period for the first day that the monitored living being spent in atrial fibrillation;
calculating from the obtained data a maximum, a minimum, and an average heart rate for the total time period for the first day that the monitored living being did not spend in atrial fibrillation; and
wherein adding to the patient report information includes adding information related to:
the maximum, the minimum, and the average heart rate calculated for the total time period that the monitored living being spent in atrial fibrillation; and
the maximum, the minimum, and the average heart rate calculated for the total time period that the monitored living being did not spend in atrial fibrillation.

5. The machine-implemented method of claim 4, wherein adding to the patient report information includes adding information related to a chart, the information including:
a graph, including a first axis representing heart rate and a second axis representing date of monitoring;
a first bar on the graph having a dimension parallel to the first axis;

the first bar having a first end proximal to the second axis and a second end distal to the second axis, wherein the first end represents the minimum heart rate and the second end represents the maximum heart rate calculated for the total time period that the monitored living being spent in cardiac arrhythmia;

a first indicator on the first bar for indicating the average heart rate calculated for the total time period that the monitored living being spent in cardiac arrhythmia;

a second bar on the graph having a dimension parallel to the first axis;

the second bar having a first end proximal to the second axis and a second end distal to the second axis, wherein the first end represents the minimum heart rate and the second end represents the maximum heart rate calculated for the total time period that the monitored living being did not spend in atrial fibrillation; and a second indicator on the second bar for indicating the average heart rate calculated for the total time period that the monitored living being did not spend in atrial fibrillation.

6. The machine-implemented method of claim 5, wherein adding information related to a chart includes adding information related to the first and second indicator wherein the first indicator has a different color or shape than the second indicator.

7. The machine-implemented method of claim 1, further comprising:

determining a total time period of monitoring for each of a second or more days;

calculating from the obtained data a proportion of the total time period that the monitored living being spent in for each of the second or more days; and wherein adding information to the patient report includes adding information related to:

the total time period of monitoring for each of the second or more days; and the proportion of the total time period that the monitored living being spent in atrial fibrillation for each of the second or more days.

8. The machine-implemented method of claim 7, further comprising:

calculating from the obtained data a proportion of the total time period that the monitored living being did not spend in atrial fibrillation for each of the second or more days; and wherein adding to the patient report information includes adding information related to the proportion of the total time period that the monitored living being did not spend in atrial fibrillation for each of the second or more days.

9. The machine-implemented method of claim 1, further comprising:

receiving human assessment data associated with the atrial fibrillation events; and modifying the percentage of the total time period of monitoring for the first day that the monitored living being spent in atrial fibrillation based on the human assessment data.

10. The machine-implemented method of claim 1, further comprising calculating one or more of: a maximum heart rate for the total time period that the monitored living being spent in atrial fibrillation, a longest atrial fibrillation episode, an average heart rate for the total time period that the monitored living being spent in atrial fibrillation, an average heart rate for a total time period that the monitored living being did not spend in atrial fibrillation; and wherein adding to the patient report information includes adding information related to one or more of: the total time monitored, the total time that the monitored living being spent in atrial fibrillation, the maximum heart rate for the total time period that the monitored living being spent in atrial fibrillation, the longest atrial fibrillation episode, the average heart rate for the total time period that the monitored living being spent in atrial fibrillation, and the average heart rate for the total time period that the monitored living being did not spend in atrial fibrillation.

11. The machine-implemented method of claim 1, further comprising:

determining a cumulative total time period of monitoring for the first and a second or more days;

calculating from the obtained data a cumulative proportion of the cumulative total time period that the monitored living being spent in atrial fibrillation for the first and second or more days; and wherein adding information to the patient report includes adding information related to:

the cumulative total time period for the first and second or more days; and the cumulative proportion of the cumulative total time period that the monitored living being spent in atrial fibrillation for the first and second or more days.

12. The method of claim 1, further comprising adding to the patient report a diagnosis associated with the selected portion of the ECG data.

13. The method of claim 12, wherein the selected portion of the ECG data is selected to be representative of the primary type of arrhythmia fibrillation event that the monitored living being experienced during the day.

14. The method of claim 12, wherein the selected portion of the ECG data is automatically selected.

15. The method of claim 14, further comprising adding to the patient report an indication of the highest heart rate measured during atrial fibrillation.

16. The method of claim 12, wherein the selected portion of the ECG data is selected by the monitored living being.

17. The method of claim 12, further comprising adding to the graph of the selected portion of the ECG data a time stamp indicating a time corresponding to the selected portion of the ECG data.

18. The method of claim 17, further comprising adding to the graph an indication of an activity of the monitored living being at the time corresponding to the selected portion of the ECG data.

19. The method of claim 1, wherein the patient report comprises a graph displaying time between on-set and off-set of the atrial fibrillation event.

20. A system comprising:

one or more computers; and a non-transitory computer-readable storage device having a computer program product encoded therein, the computer program product operable to cause the one or more computers to perform operations comprising:

obtaining ECG data associated with atrial fibrillation events and heart rate in a monitored living being by integrating atrial fibrillation, taking into account number and duration of atrial fibrillation episodes, wherein the duration is calculated as time between on-set and off-set of the atrial fibrillation event;

determining, from the obtained ECG data, a total time period of monitoring;

calculating a total time period that the monitored living being spent in atrial fibrillation for a first day by integrating atrial fibrillation episodes, taking into account number and duration of the atrial fibrillation episodes, wherein the duration of an atrial fibrillation episode is calculated as time between onset and offset of such atrial fibrillation episode, wherein the time period of monitoring comprises a plurality of contiguous, non-overlapping, equal-length, discrete time intervals, each time interval of the plurality of time intervals having a duration of ten minutes;

flagging each time interval, of the plurality of time intervals, in which an atrial fibrillation event was detected;

calculating, from the total time period of monitoring and the total time period that the monitored living being spent in atrial fibrillation for the first day, a percentage of the total time period of monitoring for the first day that the monitored living being spent in atrial fibrillation;

generating for display a patient report, including adding to the patient report information indicating including:

a plurality of blocks, each block representing a particular flagged time interval, and, on a common time scale, average heart rate for each time interval of the plurality of time intervals, whether or not flagged, and wherein a position of each block on the time scale represents a time at which a flagged time interval occurred and wherein a length of each block along the common time scale represents a duration of the flagged time interval represented by the block, and wherein the sum of the durations of the flagged time intervals exceeds the total time period that the living being spent in atrial fibrillation for the first day;

information indicating the total time period of monitoring for the first day; and a bar graph representing the percentage of the total time period of monitoring for the first day that the monitored living being spent in cardiac arrhythmia; atrial fibrillation, wherein the bar graph includes a first area having a first appearance, and a second area having a second appearance, wherein the ratio of the first area to the second area is equal to the ratio of the total time period that the living being spent in atrial fibrillation for the first day to the total time period that the living being did not spend in atrial fibrillation for the first day;

information indicating an average heart rate during the total time period that the living being spent in atrial fibrillation for the first day; and information indicating an average heart rate during the total time period that the living being did not spend in atrial fibrillation for the first day;

selecting a portion of the ECG data corresponding to one of the atrial fibrillation events; and adding to the patient report a graph of the selected portion of the ECG data.

21. The system of 20, wherein the non-transitory computer-readable storage device is further operable to cause the one or more computers to perform operations compromising:

calculating, from the total time period of monitoring and the total time period that the monitored living being spent in atrial fibrillation for the first day, a percentage of the total time period of monitoring for the first day that the monitored living being did not spend in atrial fibrillation; and wherein adding to the patient report information includes adding to the patient report information indicating the percentage of the total time period of monitoring for the first day that the monitored living being did not spend in atrial fibrillation.

22. The system of claim 21 wherein adding to the patient report information includes adding information related to a chart, the information including:

a graph, including a first axis representing time and a second axis representing date;

a bar on the graph having a dimension parallel to the first axis wherein a length of the dimension depicts the total time period of monitoring for the first day;

a first color on the bar and a second color on the bar;

wherein the amount of the first color with respect to the second color is proportional to the percentage of the total time period of monitoring for the first day that the monitored living being spent in atrial fibrillation; and wherein the amount of the second color with respect to the first color is proportional to the percentage of the total time period of monitoring for the first day that the monitored living being did not spend in atrial fibrillation.

23. The system of claim 20, wherein the non-transitory computer-readable storage device is further operable to cause the one or more computers to perform operations comprising:

determining a total time period of monitoring for each of a second or more days;

calculating from the obtained data a proportion of the total time period that the monitored living being spent in atrial fibrillation for each of the second or more days; and wherein adding information to the patient report includes adding information related to:

the total time period for each of the second or more days; and the proportion of the total time period that the monitored living being spent in atrial fibrillation for each of the second or more days.

24. The system of 23, wherein the non-transitory computer-readable storage device is further operable to cause the one or more computers to perform operations compromising:

calculating from the obtained data a proportion of the total time period that the monitored living being did not spend in atrial fibrillation for each of the second or more days; and wherein adding to the patient report information includes adding information related to the proportion of the total time period that the monitored living being did not spend in atrial fibrillation for each of the second or more days.

25. The system of claim 20, wherein the non-transitory computer-readable storage device is further operable to cause the one or more computers to perform operations comprising:

receiving human assessment data associated with the atrial fibrillation events; and modifying the proportion percentage of the total time period of monitoring for the first day that the monitored living being spent in atrial fibrillation based on the human assessment data.

26. The system of claim 20, wherein the non-transitory computer-readable storage device is further operable to cause the one or more computers to perform operations comprising:
 calculating a longest episode; and
 wherein adding to the patient report information includes adding information related to one or more of:
 the total time monitored;
 the total time that the monitored living being spent in atrial fibrillation;
 the maximum heart rate for the total time period that the monitored living being spent in atrial fibrillation;
 a longest episode;
 the average heart rate for the total time period that the monitored living being spent in atrial fibrillation; and
 the average heart rate for the proportion of the total time period that the monitored living being did not spend in atrial fibrillation.

27. The system of claim 20, wherein the non-transitory computer-readable storage device is further operable to cause the one or more computers to perform operations comprising:
 determining a cumulative total time period of monitoring for the first and a second or more days;
 calculating from the obtained data a cumulative proportion of the cumulative total time period that the monitored living being spent in atrial fibrillation for the first and the second or more days; and
 wherein adding information to the patient report includes adding information related to:
 the cumulative total time period for the first and the second or more days; and
 the cumulative proportion of the total time period that the monitored living being spent in atrial fibrillation for the first and the second or more days.

28. The system of claim 20, wherein the patient report comprises a graph displaying time between on-set and off-set of the atrial fibrillation event.

29. A machine implemented machine-implemented method comprising:
 obtaining ECG data associated with atrial fibrillation events and heart rate in a monitored living being;
 determining, from the obtained ECG data, a total time period of monitoring;
 calculating a total time period that the monitored living being spent in atrial fibrillation for a plurality of days by integrating atrial fibrillation, taking into account number and duration of atrial fibrillation episodes, wherein the duration is calculated as time between on-set and off-set of the atrial fibrillation event, wherein the time period of monitoring comprises a plurality of contiguous, non-overlapping, equal-length, discrete time intervals, each time interval of the plurality of time intervals having a duration of ten minutes;
 flagging each time interval, of the plurality of time intervals, in which an atrial fibrillation event was detected;
 calculating, from the total time period of monitoring and the total time period that the monitored living being spent in atrial fibrillation for each of the plurality of days, a percentage of the total time period of monitoring that the monitored living being spent in atrial fibrillation and a percentage of the total time period of monitoring that the monitored living being did not spend in atrial fibrillation;
 generating, by a computer, for display a patient report that includes including adding information to a single chart, wherein the information indicates chart:
 a plurality of blocks, each block representing a particular flagged time interval, and, on a common time scale, average heart rate for each time interval of the plurality of time intervals, whether or not flagged, and wherein a position of each block on the time scale represents a time at which a flagged time interval occurred and wherein a length of each block along the common time scale represents a duration of the flagged time interval represented by the block, and wherein the sum of the durations of the flagged time intervals exceeds the total time period that the living being spent in atrial fibrillation for the plurality of days;
 information indicating the total time period of monitoring for each of the plurality of days;
 a plurality of bar graphs, each bar graph associated with a particular day among the plurality of days, wherein each bar graph
 includes information indicating the percentage of the total time period of monitoring for each of the associated day among the plurality of days that the monitored living being spent in atrial fibrillation;
 includes information indicating the percentage of the total time period of monitoring for each of the associated day among the plurality of days that the monitored living being did not spend in cardiac arrhythmia; atrial fibrillation; and
 includes a first area having a first appearance, and a second area having a second appearance, wherein the ratio of the first area to the second area is equal to the ratio of the total time period that the living being spent in atrial fibrillation for the associated day to the total time period that the living being did not spend in atrial fibrillation for the associated day;
 information indicating an average heart rate during the total time period that the living being spent in atrial fibrillation for each of the plurality of days; and
 information indicating an average heart rate during the total time period that the living being did not spend in atrial fibrillation for each of the plurality of days;
 selecting a portion of the ECG data corresponding to one of the atrial fibrillation events; and
 adding to the patient report a graph of the selected portion of the ECG data.

30. The machine implemented method of claim 29, wherein generating for display a patient report that includes adding information to a single chart,
 wherein the information indicates the percentage of the total time period of monitoring for the plurality of days that the monitored living being spent in atrial fibrillation, and the percentage of the total time period of monitoring for the plurality of days that the monitored living being did not spend in atrial fibrillation further comprises
 generating for display a patient report that includes adding information to a single chart, wherein the information and cumulative percentage of the total time period of monitoring for all of the plurality of days that the monitored living being spent in atrial fibrillation further; and summary statistical data for the cumulative proportion and a cumulative percentage of the total time period for each of the plurality of days that the monitored living being did not spend in atrial fibrillation.

31. The machine-implemented method of claim 29, wherein adding information to a single chart comprises adding information related to:
- a graph, including a first axis representing a duration of time and a second axis representing date;
- a bar for each of the plurality of days on the graph, each having a dimension parallel to the first axis wherein a length of the dimension depicts the total time period of monitoring for each of the plurality of days;
- a first color on each bar and a second color on each bar;
- wherein the amount of the first color with respect to the second color on each bar is proportional to the percentage of the total time period of monitoring for the each of the plurality of days that the monitored living being spent in atrial fibrillation; and
- wherein the amount of the second color with respect to the first color on each bar is proportional to the percentage of the total time period of monitoring for each of the plurality of days that the monitored living being did not spend in atrial fibrillation.

32. The method of claim 29, wherein the patient report comprises a graph displaying time between on-set and off-set of the atrial fibrillation event.

33. A system comprising:
- a monitoring device configured to obtain physiological data for a living being and to generate annotation data indicative of atrial fibrillation events based on the physiological data for a total time period; and
- a processing system configured to:
- obtain the annotation data via a communication channel from the monitoring device wherein the data comprises integrating atrial fibrillation, taking into account number and duration of atrial fibrillation episodes, wherein the duration is calculated as time between on-set and off-set of the atrial fibrillation event,
- determine, from the annotation data, a total monitored time period and a total time period that the living being spent in atrial fibrillation for a plurality of days, wherein the total monitored time period comprises a plurality of contiguous, non-overlapping, equal-length, discrete time intervals, each time interval of the plurality of time intervals having a duration of ten minutes;
- flag each time interval, of the plurality of time intervals, in which an atrial fibrillation event was detected;
- select a portion of the physiological data corresponding to one of the atrial fibrillation events, and
- generate, for display based on the total monitored time period and the total time period that the living being spent in atrial fibrillation for the plurality of days, a daily patient report that includes
- a chart showing including
- a bar graph representing
- the percentage of the total monitored time period that the living being spent in atrial fibrillation for the plurality of days; and
- the percentage of the total monitored time period that the living being did not spend in atrial fibrillation for the plurality of days, wherein the bar graph includes a first area having a first appearance, and a second area having a second appearance, wherein the ratio of the first area to the second area is equal to the ratio of the total time period that the living being spent in atrial fibrillation for the plurality of days to the total time period that the living being did not spend in atrial fibrillation for the plurality of days;
- information indicating an average heart rate during the total time period that the living being spent in atrial fibrillation for the plurality of days;
- and
- information indicating an average heart rate during the total time period that the living being did not spend in atrial fibrillation for the plurality of days;
- and
- a chart showing the selected portion of the physiological data.

34. The system of claim 33, wherein the chart showing a percentage of a total monitored time period that the living being spent in atrial fibrillation for a plurality of days and a percentage of the total monitored time period that the living being did not spend in atrial fibrillation for the plurality of days further comprises a chart showing a percentage of a total monitored time period that the living being spent in atrial fibrillation for each of a plurality of days and a percentage of the total monitored time period that the living being did not spend in atrial fibrillation for each of the plurality of days.

35. The system of claim 33, wherein the chart showing a percentage of a total monitored time period that the living being spent in atrial fibrillation for a plurality of days and a percentage of the total monitored time period that the living being did not spend in atrial fibrillation for the plurality of days further comprises a chart showing a cumulative percentage of a total monitored time period that the living being spent in atrial fibrillation for the plurality of days and a cumulative percentage of the total monitored time period that the living being did not spend in atrial fibrillation for the plurality of days.

36. The system of claim 33, wherein the processing system is further configured to receive a request for the physiological data and to obtain the physiological data from the monitoring device.

37. The system of claim 36, wherein the physiological data includes ECG data and heart rate data.

38. The system of claim 33, wherein the processing system is configured to receive alterations in the annotation data.

39. The system of claim 20, wherein the patient report comprises a graph displaying time between on-set and off-set of the atrial fibrillation event.

* * * * *